(12) United States Patent
Myers et al.

(10) Patent No.: US 8,057,425 B1
(45) Date of Patent: Nov. 15, 2011

(54) SYSTEM FOR A PORTABLE, HANDS-FREE BREAST PUMP AND METHOD OF USING THE SAME

(75) Inventors: Kenneth E. Myers, Marietta, GA (US);
Ellen Lundy, Woodstock, GA (US);
Drew F. Meincke, Woodstock, GA (US);
Sharon Birdseye, Marietta, GA (US)

(73) Assignee: Medela Holding AG, Baar (CH)

( * ) Notice: Subject to any disclaimer, the term of this patent is extended or adjusted under 35 U.S.C. 154(b) by 0 days.

(21) Appl. No.: 12/845,860

(22) Filed: Jul. 29, 2010

Related U.S. Application Data

(63) Continuation of application No. 11/743,949, filed on May 3, 2007, now Pat. No. 7,789,865, which is a continuation of application No. 10/173,655, filed on Jun. 19, 2002, now Pat. No. 7,223,255.

(60) Provisional application No. 60/298,895, filed on Jun. 19, 2001.

(51) Int. Cl.
*A61M 1/06* (2006.01)
(52) U.S. Cl. ........................................................ 604/74
(58) Field of Classification Search .............. 604/74–75, 604/385.06–385.07, 388, 345–346, 326; 450/36–37
See application file for complete search history.

(56) References Cited

U.S. PATENT DOCUMENTS

| | | | |
|---|---|---|---|
| 4,941,433 A | 7/1990 | Hanauer | |
| 4,964,851 A | 10/1990 | Larsson | |
| 5,358,476 A | 10/1994 | Wilson | |
| 5,571,084 A | 11/1996 | Palmer | |
| 5,590,648 A | 1/1997 | Mitchell et al. | |
| 5,676,525 A | 10/1997 | Berner et al. | |
| 5,680,978 A | 10/1997 | Pinion | |
| 5,776,098 A | 7/1998 | Silver et al. | |
| 6,110,140 A | 8/2000 | Silver | |
| 6,247,996 B1 * | 6/2001 | Fields | 450/36 |
| 6,328,082 B1 | 12/2001 | Lafond | |
| 6,379,327 B2 * | 4/2002 | Lundy | 604/74 |
| 6,427,475 B1 | 8/2002 | DeFelice et al. | |
| 6,440,100 B1 * | 8/2002 | Prentiss | 604/74 |
| 6,461,324 B1 | 10/2002 | Schlensog | |

(Continued)

FOREIGN PATENT DOCUMENTS
WO   WO/99/44650   9/1999

*Primary Examiner* — Nicholas D Lucchesi
*Assistant Examiner* — Melissa A Snyder
(74) *Attorney, Agent, or Firm* — McDonnell Boehnen Hulbert & Berghoff LLP

(57) ABSTRACT

A portable, hands-free and user friendly breast pump for facilitating breast-feeding, incorporates a dome-shaped housing having a servomotor mechanism; a hat-shaped flange having a chamber portion, a brim portion and an outlet, the chamber portion being formed so as to be placed over a nipple on a breast so as to define a chamber between the flange and the breast, and the brim portion being formed to surround the nipple and thereby form a suction seal therebetween; and a one-way venting element formed to operatively communicate with the chamber so as to vent pumped milk from the chamber via the outlet. The housing, the flange and the venting element are connected into an integral device held against the breast and underneath clothing so as to keep the integral device hidden. Breast milk is collected via a plastic collection bag that connects directly with the pump underneath clothing such that the milk is isolated from any contaminants in the air and may be easily stored immediately after being collected.

12 Claims, 35 Drawing Sheets

U.S. PATENT DOCUMENTS

| | | |
|---|---|---|
| 6,547,756 B1 | 4/2003 | Greter et al. |
| 2002/0062103 A1 | 5/2002 | Larsson et al. |
| 2002/0156419 A1 | 10/2002 | Silver et al. |
| 2003/0069536 A1 | 4/2003 | Greter et al. |
| 2003/0191433 A1* | 10/2003 | Prentiss .......................... 604/74 |
| 2006/0106334 A1* | 5/2006 | Jordan et al. .................... 604/74 |
| 2008/0208116 A1* | 8/2008 | Dao et al. ........................ 604/74 |

* cited by examiner

SYSTEM FOR A PORTABLE, HANDS-FREE BREAST PUMP AND METHOD OF USING THE SAME

CROSS REFERENCE TO RELATED APPLICATIONS

This application is a continuation of U.S. patent application Ser. No. 11/743,949, now U.S. Pat. No. 7,789,865, filed May 3, 2007, entitled "Breast Cup with an Internal Vacuum Chamber for a Hands-Free Breastpump," the contents of which are fully incorporated herein by reference, which is a continuation of U.S. patent application Ser. No. 10/173,655, now U.S. Pat. No. 7,223,255, filed Jun. 19, 2002, entitled "System for a Portable Hands-Free Breastpump and Method of Using the Same," the contents of which are fully incorporated herein by reference, which is a non-provisional of U.S. Application Ser. No. 60/298,895, filed Jun. 19, 2001, the contents of which are fully incorporated herein by reference.

This application is related to U.S. patent application Ser. No. 11/933,696, now U.S. Pat. No. 7,785,305, filed Nov. 1, 2007, entitled "System for Collecting Breast Milk from a Human Breast," the contents of which are fully incorporated herein by reference, which is a continuation of U.S. patent application Ser. No. 10/173,655, now U.S. Pat. No. 7,223,255, filed Jun. 19, 2002, entitled "System for a Portable Hands-Free Breastpump and Method of Using the Same," the contents of which are fully incorporated herein by reference, which is a non-provisional of U.S. Application Ser. No. 60/298,895, filed Jun. 19, 2001, the contents of which are fully incorporated herein by reference.

BACKGROUND OF THE INVENTION

1. Field of the Invention

The invention generally relates to a portable, hands-free, and visually friendly breast pump system and method for collecting milk from a breast of a nursing mother which may be hidden from view when in use. In particular, the invention may be hidden underneath the clothing of a nursing mother, which provides privacy and avoids any attention and the awkwardness experienced by the nursing mother using existing breast pumps.

2. Description of the Related Art

Breastfeeding is the best source of nutrition for a baby, and it also offers health benefits to the nursing mother. Often, the nursing mother needs to use a breast pump to collect milk. A variety of breast pumps are available. The basic types of breast pumps include manual (hand operated) pumps and electric pumps. The electric pumps may be battery and/or AC powered. Further, the electric pumps may be self-cycling or require some manual user control. U.S. Pat. No. 6,213,840 combines a manual hand pump with a breast pump support bra which supports the weight of the breast. While most hand pumps are inexpensive and portable, they are typically uncomfortable, inefficient, and difficult to clean.

Some electric pumps are not battery-operated such that the nursing mother has to be near a power outlet. Other electric pumps, such as the diaphragm pump disclosed in U.S. Pat. Nos. 6,257,847 and 6,090,065, are assembled from many parts (hoses, gaskets, valves, etc.) which are difficult to clean, wash and carry. FIG. 27 illustrates such a prior art system from the '065 patent having many parts which makes it cumbersome and difficult to use. In particular, in such a traditional breast pump, the milk has to pass through a plurality of components, such as a funnel P20, a cylindrical guiding means P22, a cap assembly P30, a reservoir P40, an inlet P62 connected to the suction assembly, etc., just to get to a container.

The website at http://www.epinions.com/kifm-Health-Nursing_and_Feeding-Breast_Pumps-All/tk_~PR001.10.5 lists many commercially available breast pumps. Most of the electric breast pumps, such as Hollister's Purely Yours™ Kit, are cumbersome and noisy, and thus very stressful for the nursing mother to use. In addition, while the nursing mother is using these breast pumps to collect milk, she cannot take care of the baby or do anything else.

Even more, these pumps share the disadvantage that the mother's breast is exposed during use (lack of privacy) and that their motors are noisy. The breast pump vest described in U.S. Pat. No. 5,571,084, although covering most of the breast, is heavy and inconvenient to wear.

Currently, there are no portable and user-friendly breast pumps capable of achieving private, quiet, easy, efficient, and effective breast-feeding.

SUMMARY OF THE INVENTION

It is a purpose of this invention to provide a portable and hands-free breast pump system that facilitates hands-free, private, quiet, easy, efficient, and effective breast-pumping.

It is another purpose of this invention to allow a nursing mother to collect milk via a breast pump hidden from view beneath clothing.

It is another purpose of this invention to allow a nursing mother to collect milk via a breast pump while nursing a baby or doing something else at the same time.

It is another purpose of this invention to provide a breast pump that has very few parts, and is easy to assemble and clean.

It is another purpose of this invention to provide a breast pump that is cost-effective and easy to transport.

It is another purpose of this invention to provide a breast pump with a vacuum chamber which also functions as a part of the vacuum mechanism.

It is still another purpose of this invention to reduce the contamination of the milk during the processing, such as collection and storage, by a breast pump system.

It is still another purpose of this invention to accurately emulate the suckling action of a baby when breast-feeding so as to facilitate the numerous benefits of breast-feeding to the mother and to the baby.

BRIEF DESCRIPTION OF THE DRAWINGS

The foregoing and additional features and characteristics of the present invention will become more apparent from the following detailed description considered with reference to the accompanying drawings in which like reference numerals designate like elements and wherein:

FIG. 8A shows an adapter for connecting a positive contacting pin to an external power supply of the invention, while

FIG. 18A shows a splint for use with the breast pump of the invention, while

DESCRIPTION OF THE PREFERRED EMBODIMENTS

Figure 1A:
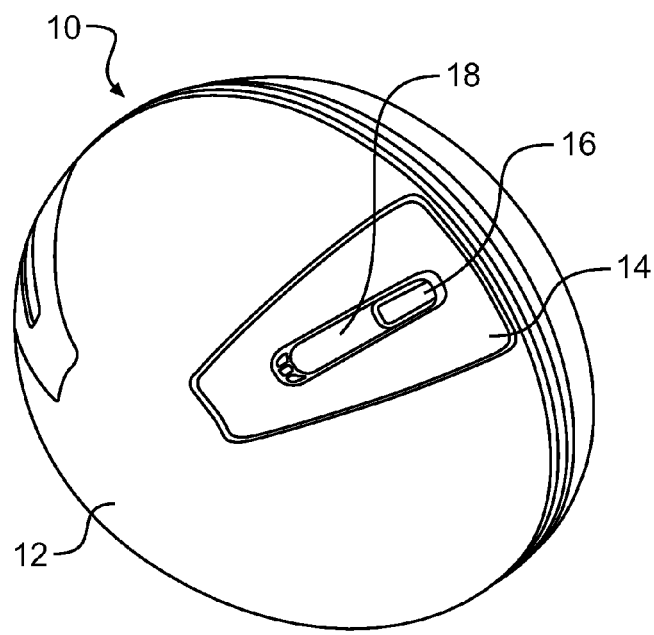
FIG. 1A is a perspective view showing the front side of the breast pump according to a preferred embodiment of the invention.
Figure 1B:
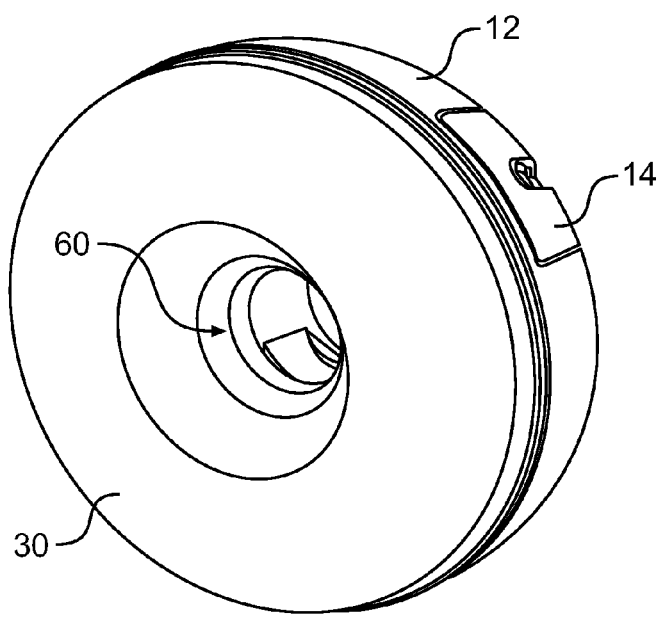
FIG. 1B is a perspective view showing the rear side of the breast pump according to the first embodiment of the invention.

With reference to the figures, like reference characters will be used to indicate like elements throughout the several embodiments and views thereof. In particular, referring to FIGS. 1A and 1B, the breast pump 10 of the invention is embodied as a volume-displacement-type pump. FIG. 1A is a perspective view of a preferred embodiment of the present invention showing the front side of the breast pump 10 with a dome-shaped housing shell 12. The housing shell 12 gives a natural appearance of the shape of a breast when the pump 10 is concealed underneath the user's clothing. FIG. 1B is a perspective view showing the rear side of the breast pump 10.

Figure 2:
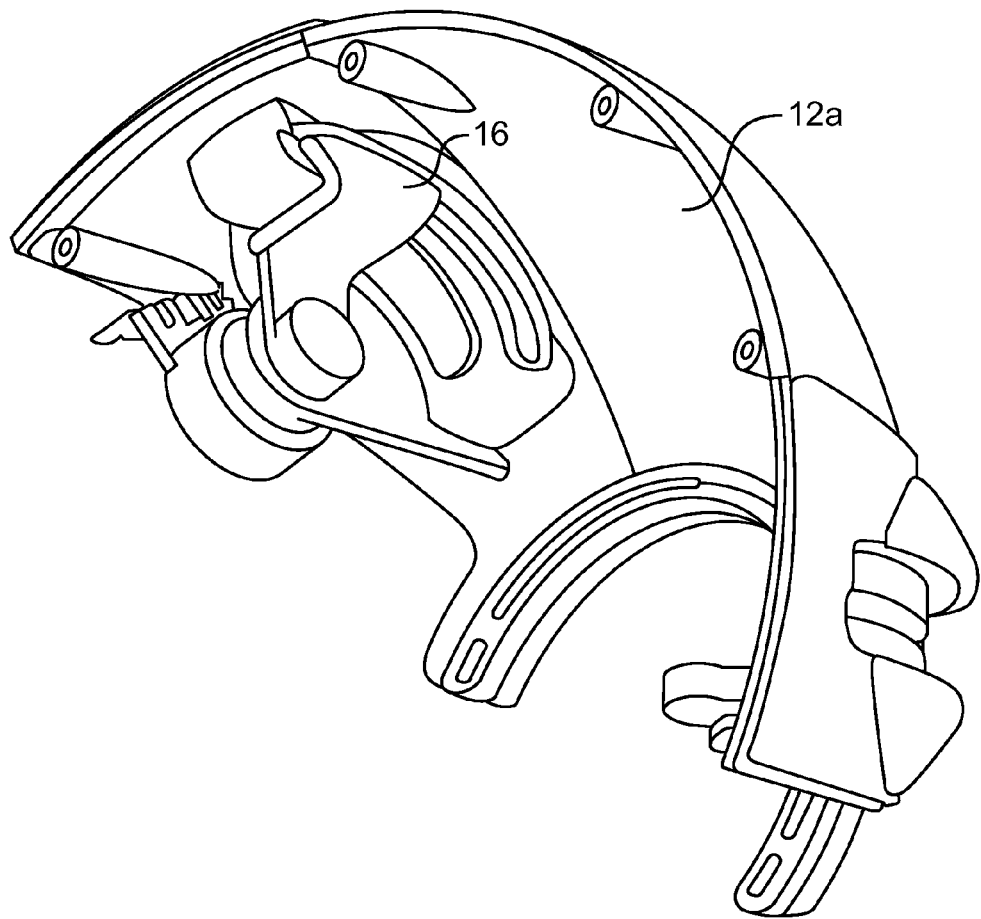
FIG. 2 is a rear view of a top housing cover of the breast pump according to the first embodiment of the invention shown in FIG. 1.

The pumping action generated by the breast pump 10 depends upon a cycle rate and a vacuum level which are controlled via an adjusting means 14. In one implementation, a user may use one finger to slide button 16 in an axial direction along the groove 18 so as to adjust the vacuum level (or range). FIG. 2 depicts the open top housing cover 12a of breast pump showing the rear side of the slide button 16 shown in FIG. 1.

Figure 3:
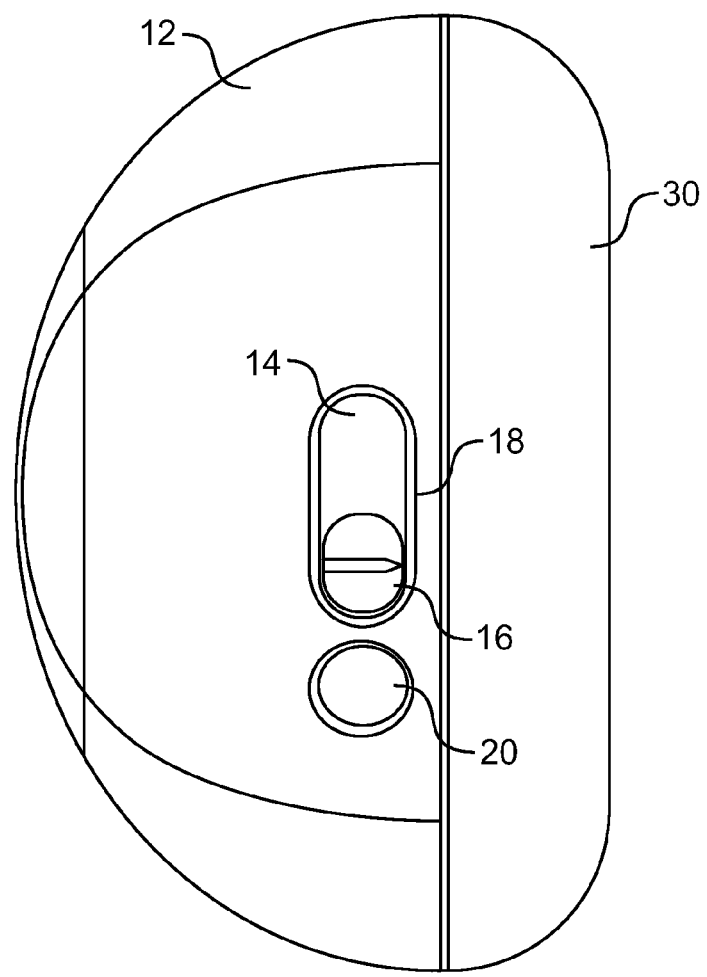
FIG. 3 is side view showing the breast pump according to a second embodiment of the invention.
Figure 4:
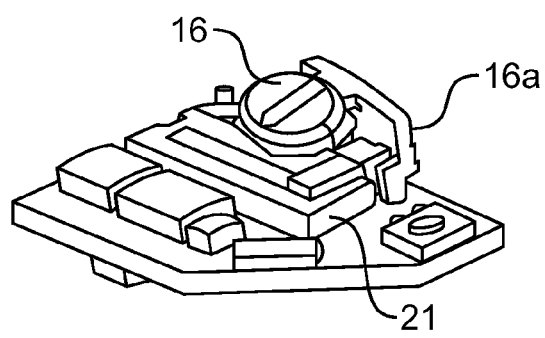
FIG. 4 shows the details of the slide button according to the second embodiment of the invention.

In a second embodiment shown in FIG. 3, the slide button 16 is configured to slide in a circumferential direction along the groove 18 so as to adjust the pumping action to continuously vary the vacuum level. A push button 20 is used to control the cycling rate by incrementally increasing the rate with each push of the button 20 up to the fastest cycling rate designed into the pump. A further push of the button 20 then rolls the increment back to the slowest cycling rate for a continuous loop operation. FIG. 4 depicts that the slide button 16 is connected to an electrical contacting base 21 with an arm 16a so as to slide the electrical contacting base 21 and vary the vacuum level.

Figure 5:
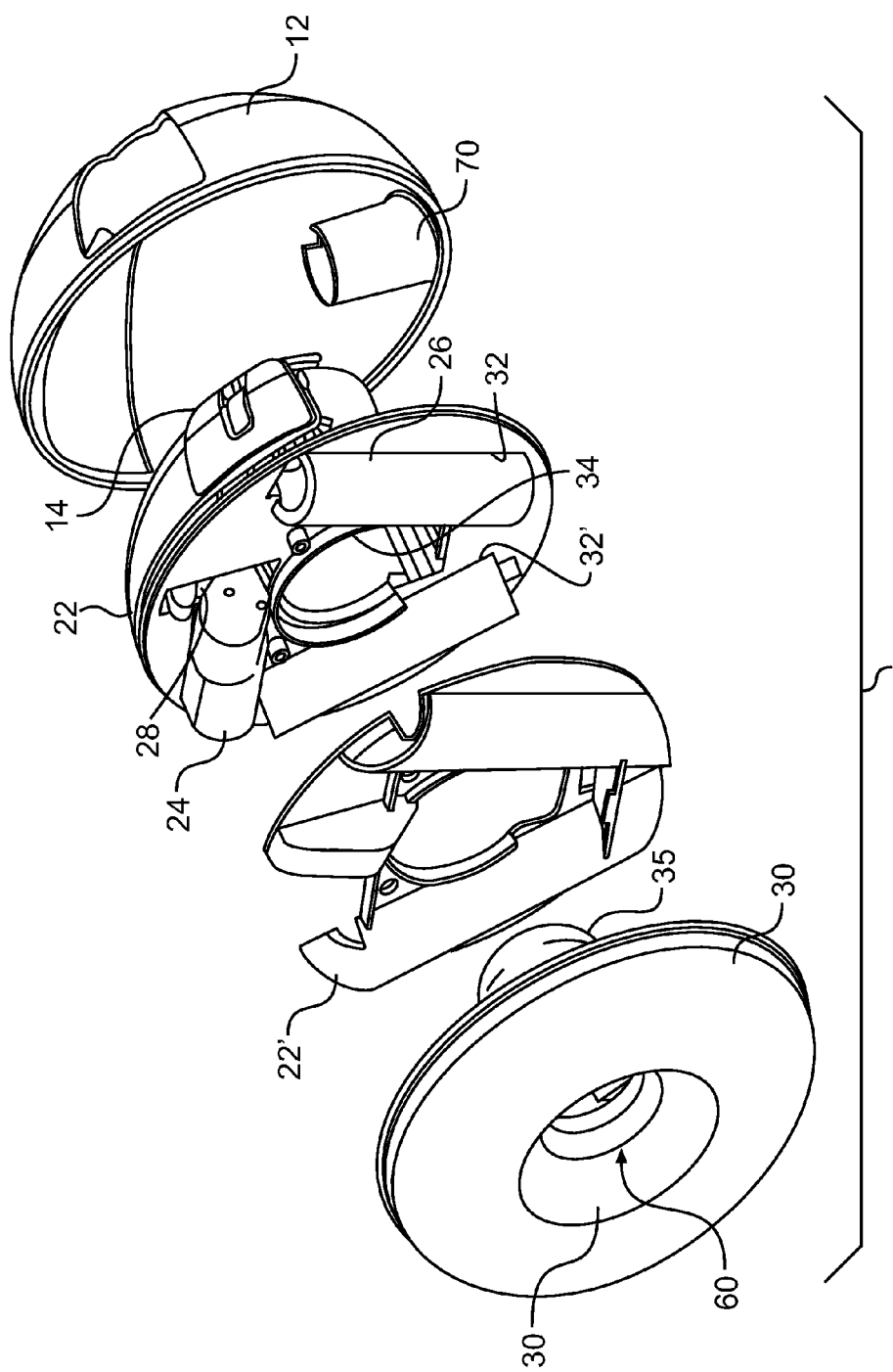
FIG. 5 is an exploded view showing the breast pump of the first embodiment of the invention.

Referring to FIG. 5, each breast pump 10 includes a housing shell 12, a central deck 22 with a servomotor mechanism 24 integrated therewith, and a straw-hat shaped breast "flange" 30 having a flange top 35. The servomotor mechanism 24 is a servomotor mechanism powered by at least one power source 26, such as two AA batteries. The central deck 22 includes a pump seat 28 for receiving the servomotor mechanism 24, two battery seats 32, 32' for receiving the batteries 26, and a tunnel 34 extending toward the housing shell 12 for guiding and receiving a piston cylinder 25 of a rear-piston lever-arm system 100 (See FIGS. 11A-11C). A central deck cover 22' is used to fixedly encase the servomotor mechanism 24 and the two batteries 26 in the central deck 22.

Figure 6:
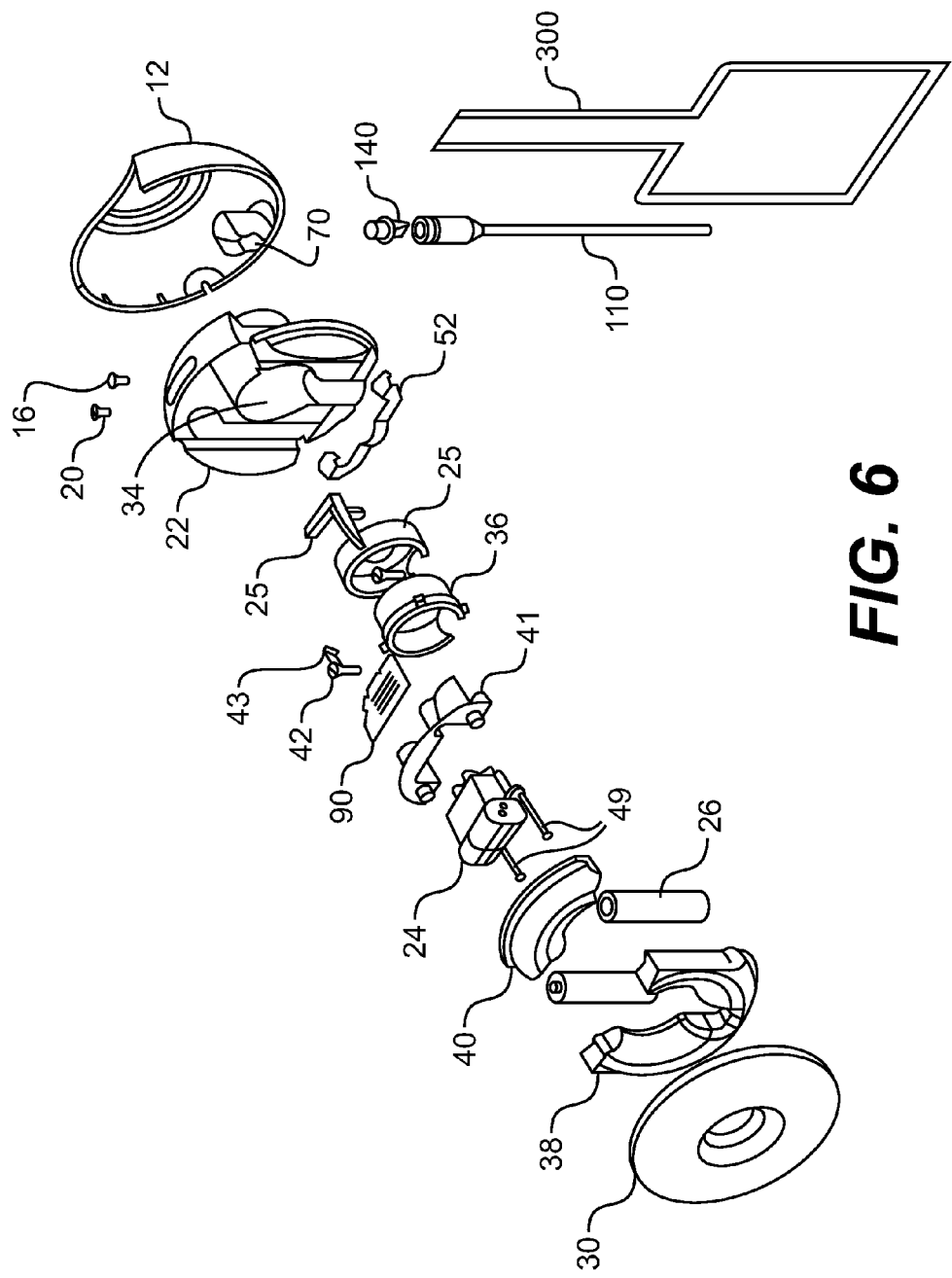
FIG. 6 is an exploded view showing the breast pump of the second embodiment in conjunction with a one-way valve and a splint.

A second embodiment of the breast pump 10 as shown in FIG. 6 is designed for a breast larger than that to which the first embodiment shown in FIG. 5 is applied. Therefore, the central deck 22 of this second embodiment of the breast pump has a larger space that allows the two batteries 26 to be positioned parallel to one another. In addition, the central deck 22 of the second embodiment incorporates other parts for other parts, such as motor cover 40, rather than the fewer integral pieces as in the first embodiment.

Specifically, the breast pump 10 of the second embodiment includes the housing shell 12, the cycling rate button 20, the vacuum level slide button 16, the central deck 22, the flange 30, the servomotor mechanism 24, and the batteries 26. In addition, the second embodiment includes a flange support 36 placed between the flange top 35 and the piston cylinder 25, a servomotor cover 40, a battery cover 38, a printed circuit assembly ("PCA")/microprocessor 90, a PCA compartment 41, a DC power jack pin 42 (positive), a DC power jack tab 43 (negative), a battery contact 52, and a pair of screws 49 (FIG. 6).

Figure 7:
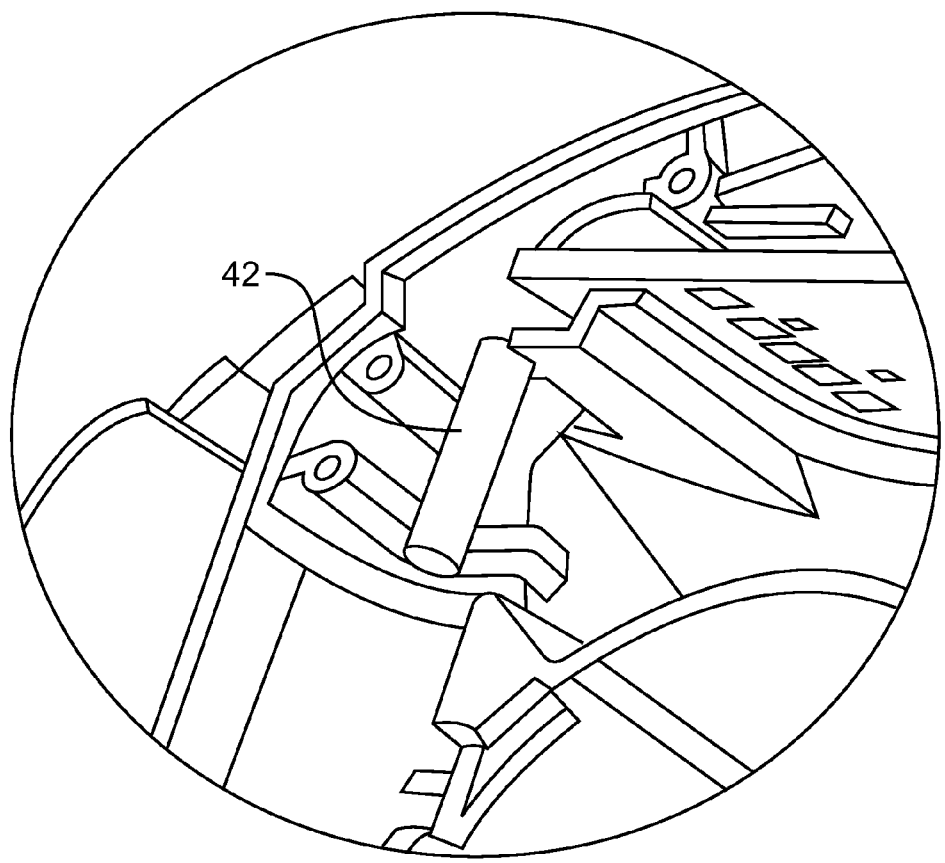
FIG. 7 is an enlarged inset view of a positive connect pin of the breast pump according to the second embodiment of the present invention.

The first embodiment of the breast pump uses traditional positive and negative contact plates with springs for receiving each battery. In the second embodiment of the breast pump, one positive contact pin 42 (FIG. 7 inset view) is used instead. Both of these configurations would be known in the art for purposes of connecting to batteries held in small compartments.

The second embodiment of the breast pump (FIG. 6) has an additional flange support 36 designed to protect against any overshooting of the strokes towards the flange top 35. The flange support 36 is fixed in place with the control deck 22, such as via a rotating lock mechanism, and then fitted around the exterior of the vacuum chamber 60 so as to have an interference fit at least around the base of the flange 30 (i.e., the 'bellows' area of the flange which creates the air displacement). The flange support 36 is an individual part of the unit assembly designed to be attached onto the flange 30. The flange support 36 not only holds the flange 30 in place during the pumping action (prevents over-pressure on the flange top 35) but also supports the vacuum chamber 60 from collapsing.

Unlike most other breast pumps which have their pump mechanisms situated outside of their breast interface elements or even at a remote distance from the breast interface element, the servomotor mechanism 24 of the invention is integrated inside the pump 10. The servomotor mechanism 24 is designed to be lightweight (for example, 0.4 oz. making each entire pump 10 weigh only 2.4 oz. without batteries or 4.2 oz. with batteries) such that it sits directly inside the pump 10 and is supported by the housing without any additional components. The pump 10 in turn is exclusively supported by the bra and the negative pressure created between the breast and the flange 30 by the servomotor mechanism 24 and the lever arm system 100. In variations of the present invention, the servomotor mechanism 24 may be substituted with an external driving mechanism, such as an electrical motor or a tethered manual pumping device, to provide the negative pressure for pumping. The implementations of such substitute devices would have those devices modularized such that they could be substituted for one another and be easy to replace.

Figure 8A:
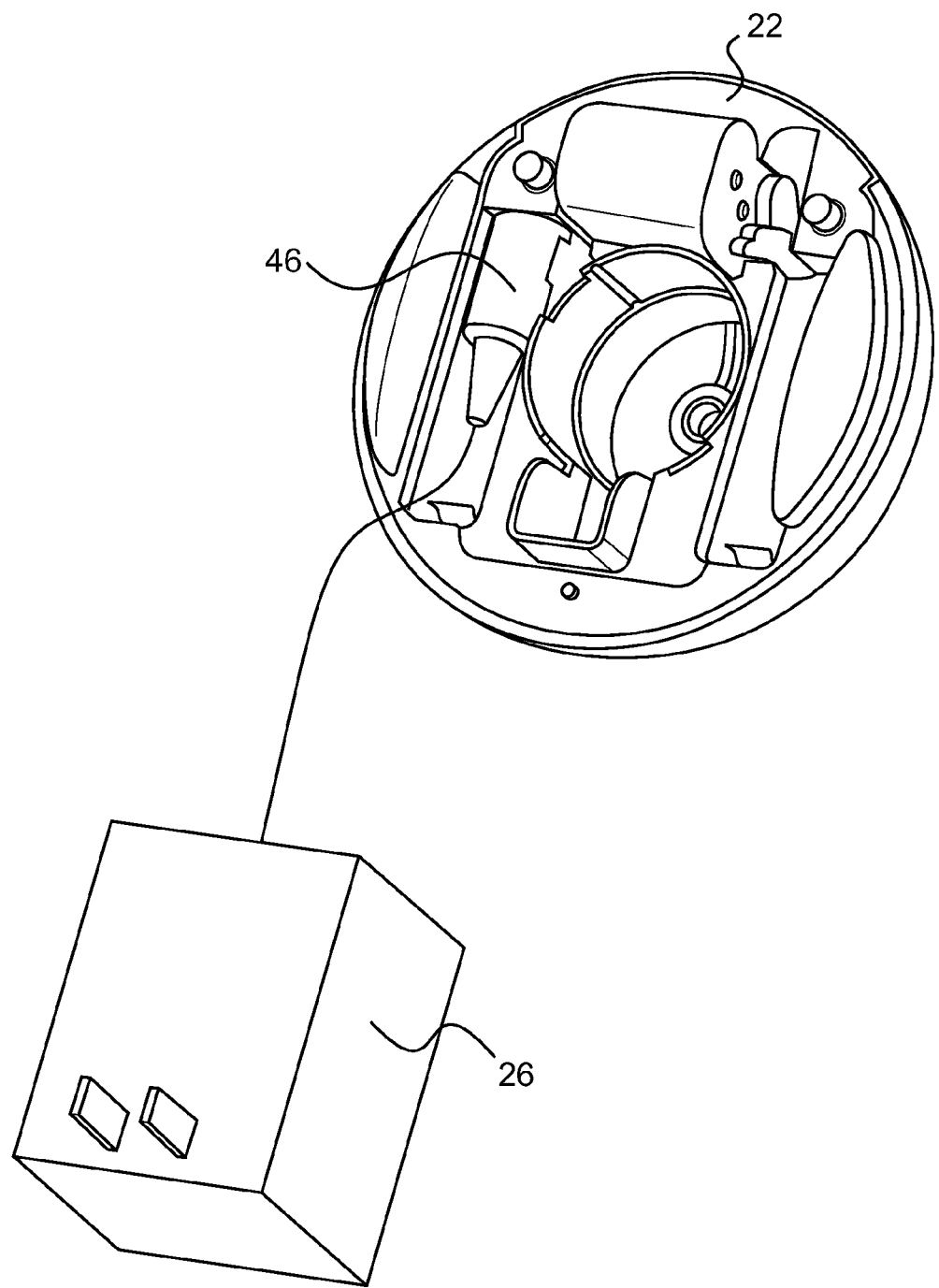
Figure 9:
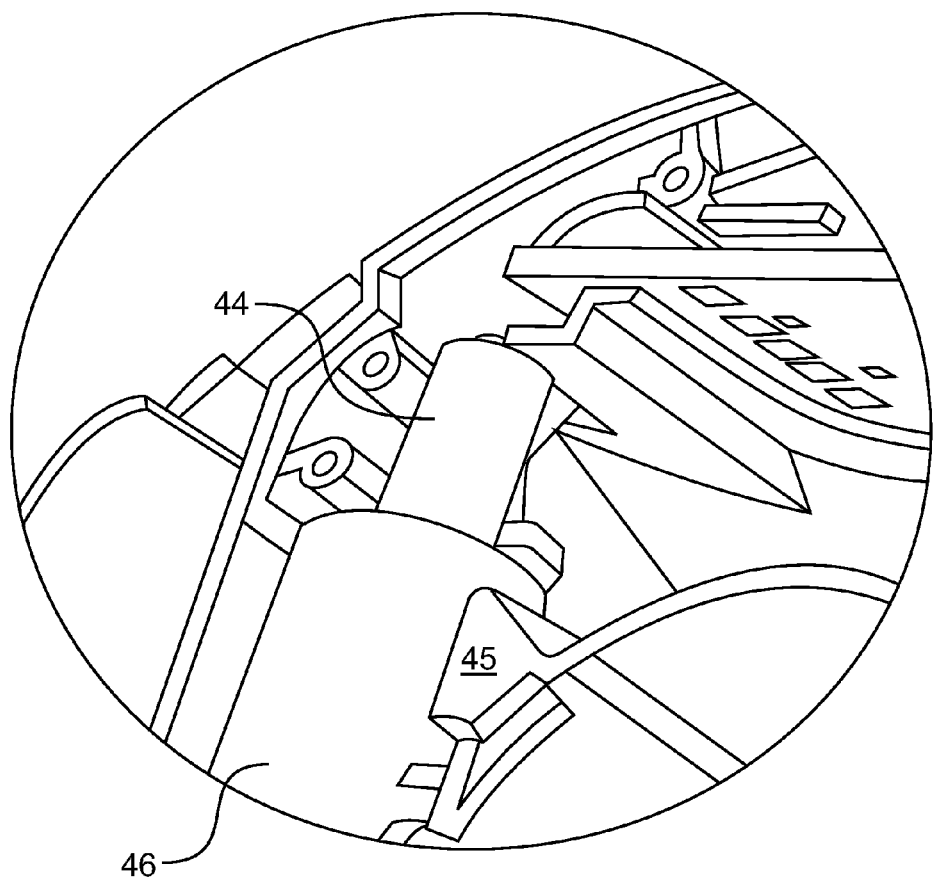
FIG. 9 is an enlarged inset view showing the connection between the external power supply of FIG. 8A and a positive contacting pin.

In a third embodiment of the breast pump, power for the external servomotor mechanism 24 is located outside the housing. As shown in FIG. 8A, an adapter 46 is used to connect a positive contacting pin to the external power supply 26 via a wire 26a. FIG. 9 shows an inset view of how the adapter 46 is attached to the positive contacting pin 44. This embodiment has the advantage of a longer-lasting power supply that can be used, for example, in an institutional setting (i.e., a hospital) or even a home setting where a more limited range of mobility is acceptable or even desired.

Figure 8B:
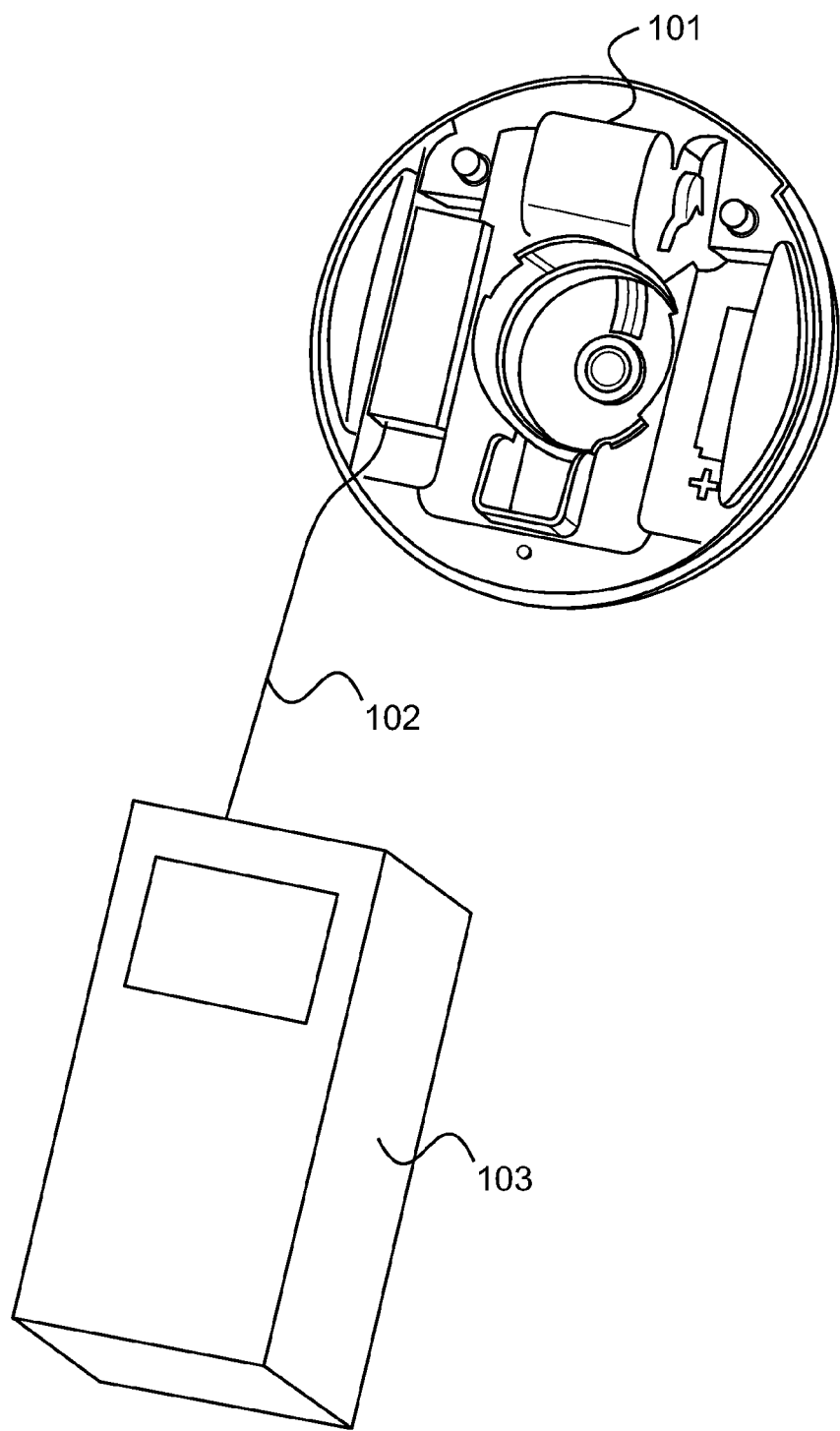
FIG. 8B shows an example of a tethered drive configuration of the present invention.

Alternatively, as shown in FIG. 8B, the servomotor mechanism 24 may be replaced by a servomechanism 24' that may be just a mechanical or pneumatic linkage 101 connected to the lever arm 21 for implementing the pumping action of the vacuum chamber 60. The linkage 101 is connected to a remote control 103 that acts as the user's control for pumping via a linkage element 103. For example, in a mechanical implementation, the linkage element 103 is a wire in a sleeve similar to that used in bicycle handbrake controls, while the control 103 is a hand- or foot-pedal that the user manipulates to move the lever arm 21 in the pump 10. Alternatively, in a pneumatic implementation, the linkage element 103 is a flexible pipe that feeds air or fluid into the linkage 101. The control 102 is also a hand- or foot-pedal that controls the flow of control air/fluid to the linkage 101 to then operate the pumping motion of the lever arm 21. The specific details for implementing either of the above-discussed alternative embodiments would be within the knowledge of those skilled in the art.

Various components of the system are formed from resiliently plastic or other resin-type materials to accomplish various purposes. For example, in order that the splint 110 be flexible so as to conform with the shape of the user's breast, and so that the overall structure of the pump 10 is lightweight, including but not limited to the housing shell 12, the housing cover 12a, the lever arm 21 and the central deck 22, these various parts are formed from plastic. Other components in the system would be formed from materials appropriate to their function as would be understood by those skilled in the art. Other materials for the various components may also be used as would be known in the art so long as the selection of such materials is not inconsistent with the structure, operation and purpose of each such component and of the present invention as a whole.

Figure 20A:
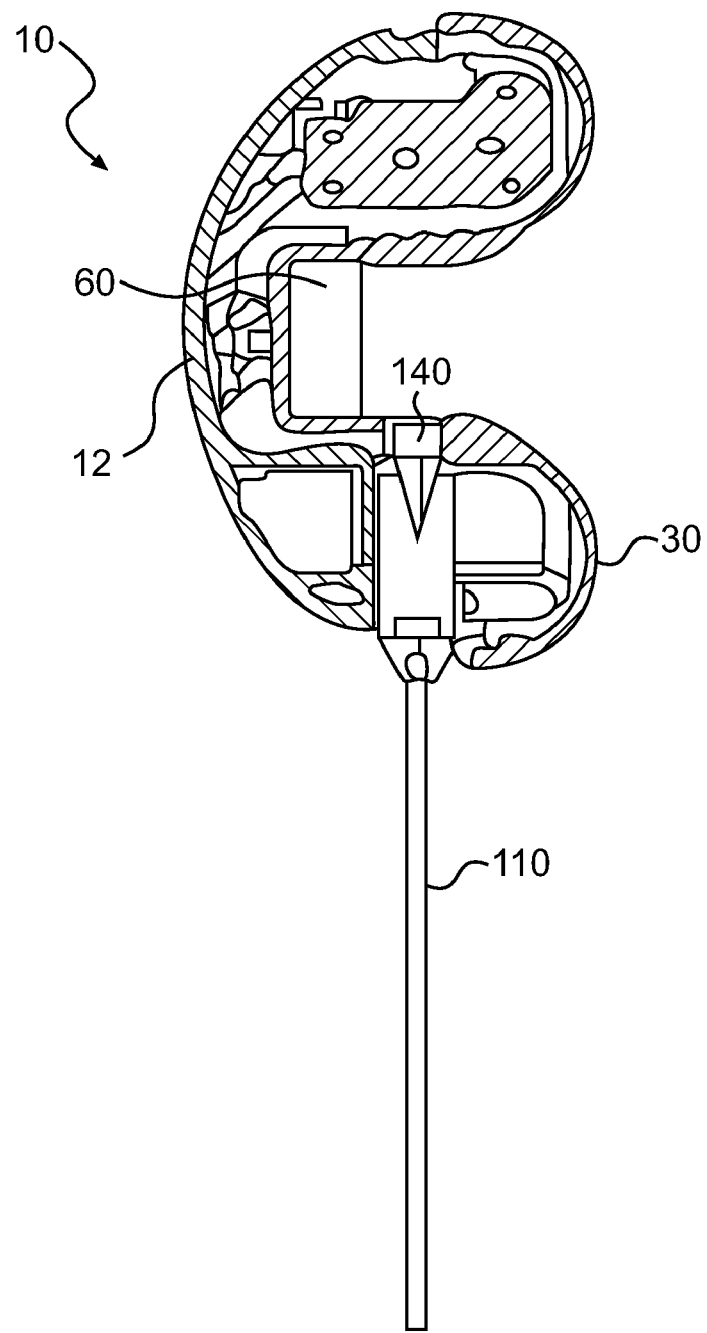
FIGS. 20A and 20B show cross-sectional views of the pump along with splint and the bag bent to conform with the contour of the user's breast and body.
Figure 20B:
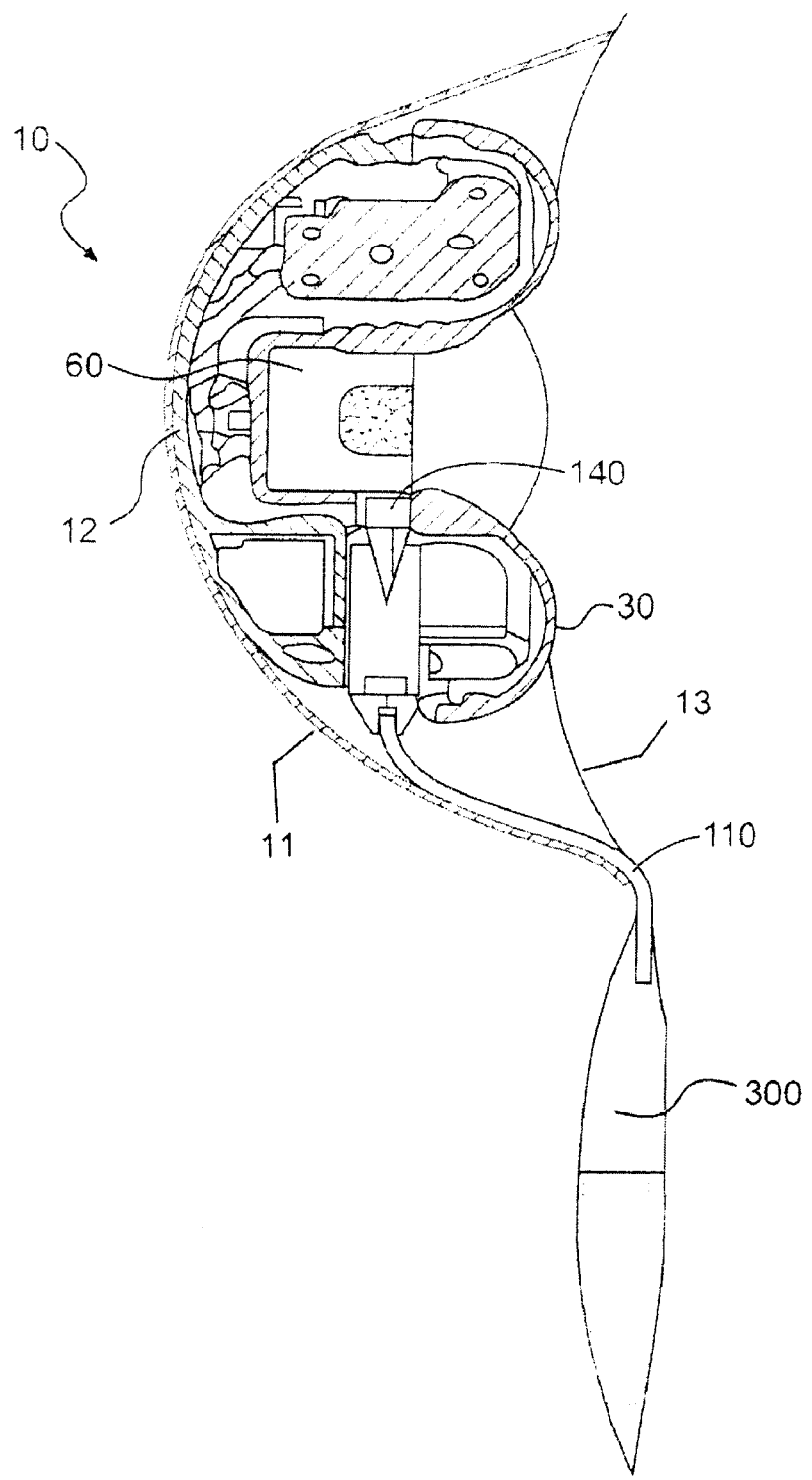

In the general operation and use of the present invention, as shown in FIGS. 20B, the pump 10 contacts the breast only with the breast flange 30, and the dome-shaped housing shell 12 does not contact the breast. A vacuum chamber 60 is defined between the breast flange 30 and the breast, and is completely isolated from the working components of the breast pump 10; the servomotor mechanism 24 is only in contact with the exterior surface of the breast flange 30. This allows the vacuum chamber 60 to be maintained at a negative air pressure while keeping the breast milk from contacting any other parts of the breast pump 10. The invention significantly reduces the number of parts that can come in contact with the milk so as to make the system easy to clean and sanitary. Further, the invention eliminates the potential of the milk co-mingling with any room air contaminants.

Figure 10A:
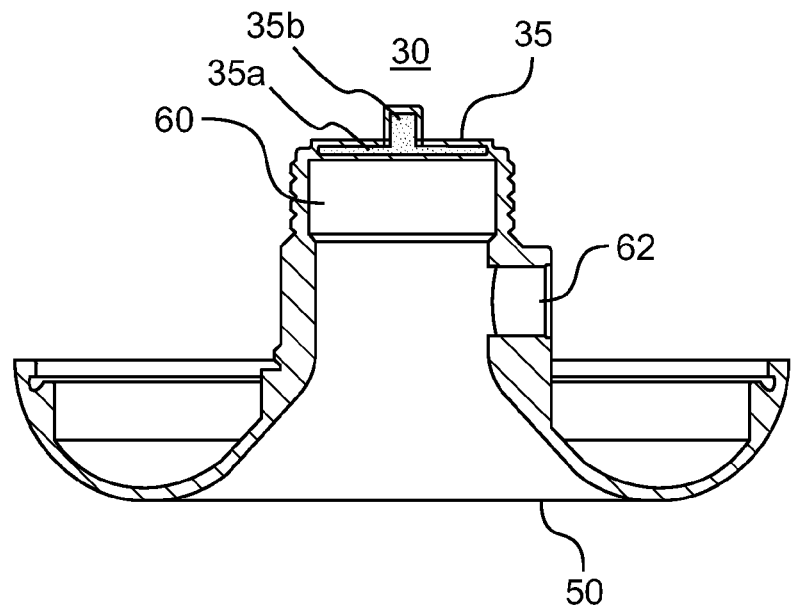
FIGS. 10A and 10B show cross-sectional views of different embodiments of the flange of the invention.
Figure 10B:
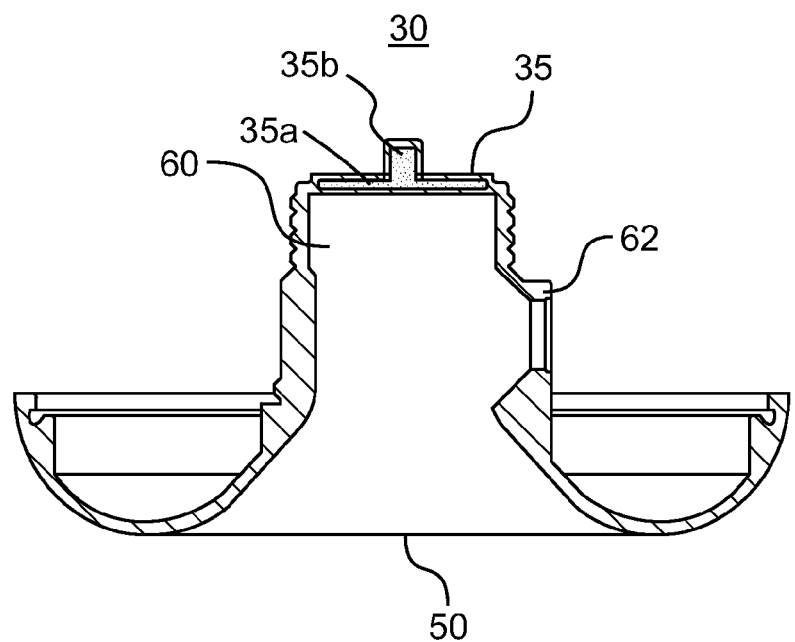

The breast flange 30 is made from silicone or other soft elastic material for interfacing directly with a breast and situated on the breast with an inlet hole 50 (See FIGS. 5, 10A and 10B). The inlet hole 50 is designed for seating a nipple and areola in a vacuum chamber 60 which is defined between the breast pump 10 and the breast. The soft breast flange 30 allows the wearer to pump milk quickly and painlessly by mimicking the baby's suckling movements when the servomotor mechanism 24 moves the flange 30, thereby triggering the female body's natural reaction to produce milk.

Figure 27:
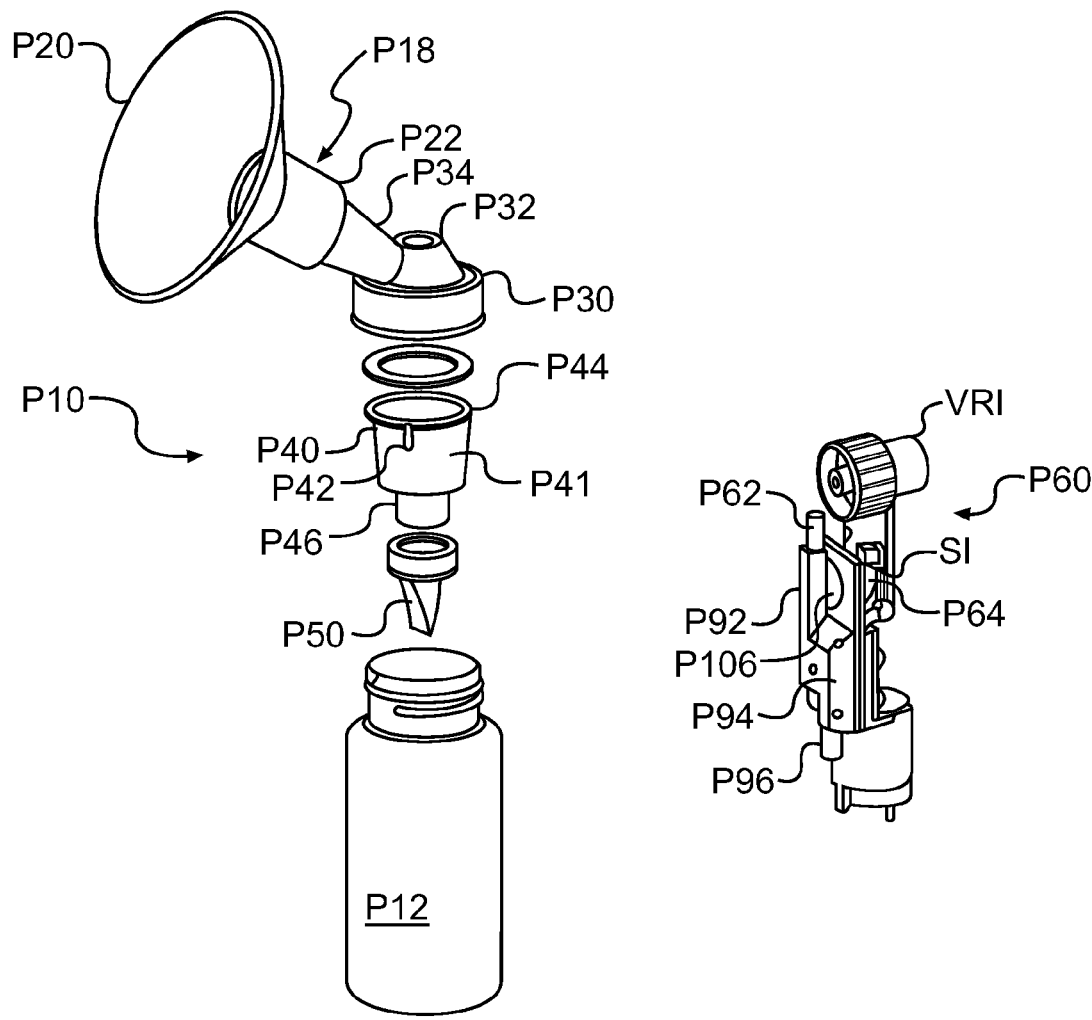
FIG. 27 is an exploded view showing the breast pump of the prior art (U.S. Pat. No. 6,090,065).

A health benefit for the user or mother derived from the invention is that, as the nerves in the nipple and areola are stimulated by the action of the invention, the pituitary gland receives a signal to release prolactin and oxytocin into mother's blood stream. Prolactin relaxes the mother and stimulates the alveoli to produce more milk. Oxytocin causes the alveoli to contract and squeezes milk into the ducts. In contrast, the traditional hard funnel breast pumps (See FIG. 27) simply pull the nipple into the rigid shaft to obtain milk. The hard shaft of the funnel is rigid and unyielding so that the suction concentrates on the nipple and creates a stinging sensation.

Varying thicknesses in the silicone flange 30 helps the breast pump 10 to attach to the breast and be compressed towards the nipple by the rear-piston lever-arm system 100 shown in FIGS. 6, 11A-11C and 13. Pumping sessions become faster by using the soft flange 30 since the milk is being removed in a more natural way than with a traditional hard funnel. As such, the milk is also better extracted from the breast to avoid any decrease of milk production due to the remaining breast milk in the breast. The milk residuals reduce hormone stimulation for milking.

As shown in FIG. 10A, the flange 30 includes an outlet 62 through which the milk drawn from the breast flows out of the flange 30. As will be discussed further herein, the milk is then directed away from the breast pump 10 and stored. In a variation of the flange 30, as shown in FIG. 10B, the outlet 62 is funnel-shaped so as to direct the milk flow out of the flange 30 and prevent the milk from flowing back towards the breast.

In at least one of the embodiments of the invention, the nipple is well seated at the back of the breast pump 10 (inside the chamber 60), where only air is directly in contact with the nipple. When the nipple is placed inside the flange 30, the nipple rests within the vacuum chamber 60 with the surface of the surrounding area of the breast in contact with the surface of the flange 30. Air compression and suction is then controllably generated to occur by virtue of the cap-shaped piston cylinder 25 being cyclically pushed toward the breast so as to physically push on the top 35 of the flange 30 (see FIG. 11A), and then released. The top 35 is formed with a relatively thin and soft side wall which has an accordion-style, contour-shape with alternating convex and concave edges formed on its surface for transferring and converting the contact pressure from the cap-shaped piston cylinder 25 to air compression and suction on the nipple. In order to strengthen the top 35 and to help in uniformly compressing the vacuum chamber 60, the top 35 may be formed with a circular, reinforcing plate 35a fixedly imbedded therein. The reinforcing plate 35a is formed with a dome-shaped alignment stub or nipple 35b on a top center portion of the plate that aligns with the alignment dome 25b of the piston cylinder 25 so as to center the vacuum chamber 60 within the piston cylinder 25. This centered alignment is especially important in keeping the vacuum chamber 60 from floating or misaligning within the piston cylinder 25 during the pumping operation.

Figure 11A:
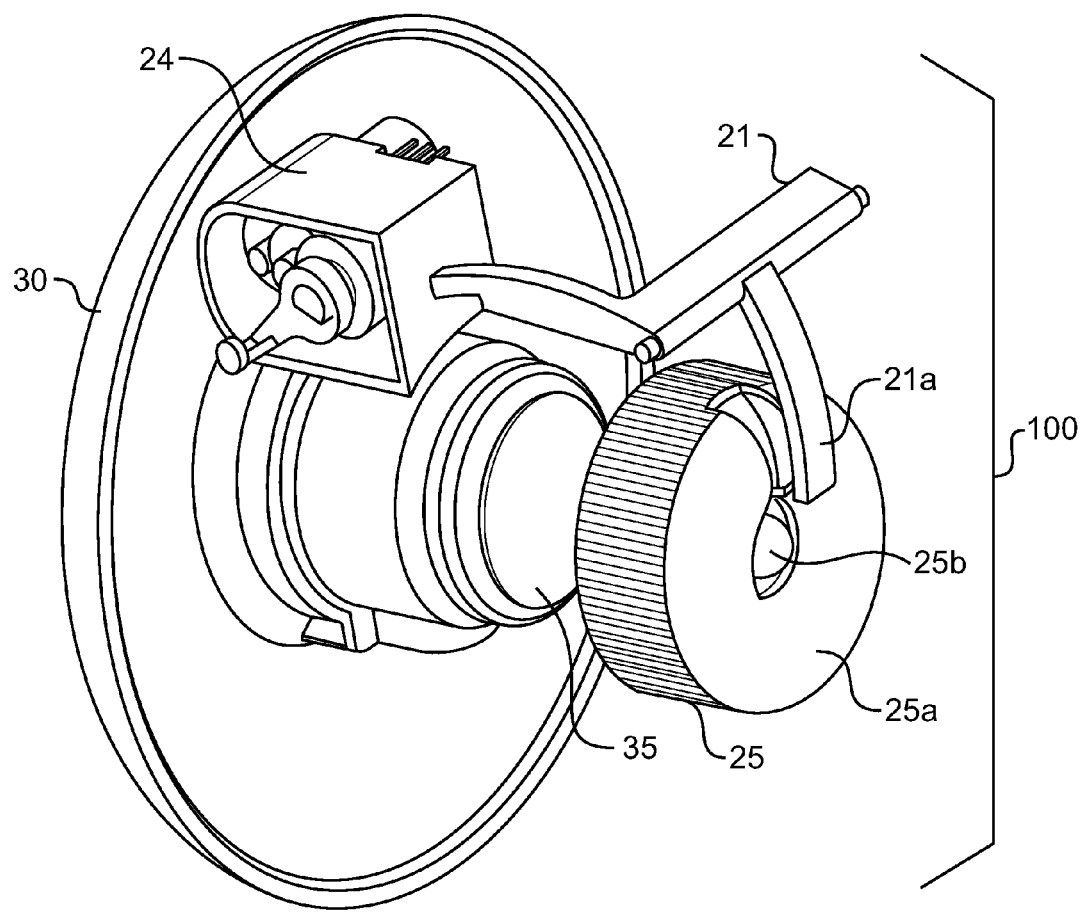
FIGS. 11A-C show a rear-piston lever-arm system of the breast pump according to the second embodiment that communicates with the servomotor mechanism so as to move linearly.
Figure 11B:
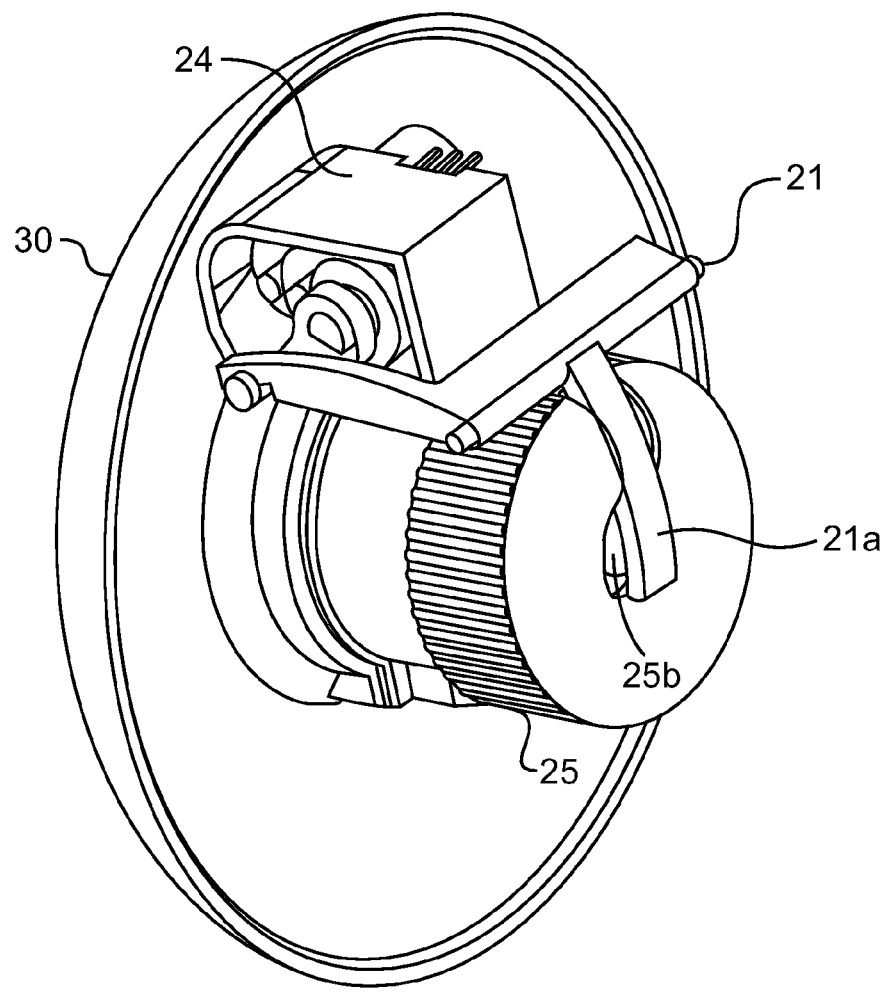

In a first embodiment of the rear-piston lever-arm system 100, as shown in the exploded view of FIG. 11A, the top of the piston cylinder 25 is shaped like a yo-yo or a doughnut without a hole. The lever arm 21 has a protrusion 21a on the top that contacts with the alignment dome 25b of the piston cylinder 25. The lever arm 21 is a projecting handle used to adjust or operate the piston cylinder 25. In particular, the-rear piston lever-arm system 100 mechanically communicates with the servomotor mechanism 24 so as to be activated by the mechanism and thereby pivotally move the lever arm 21 which then linearly moves the piston cylinder 25 along a line generally parallel with the centerline of the pump 10. Such a linear movement is depicted, wherein the start or "upstroke" position of the piston cylinder's linear movement is shown in FIG. 11B.

Figure 11C:
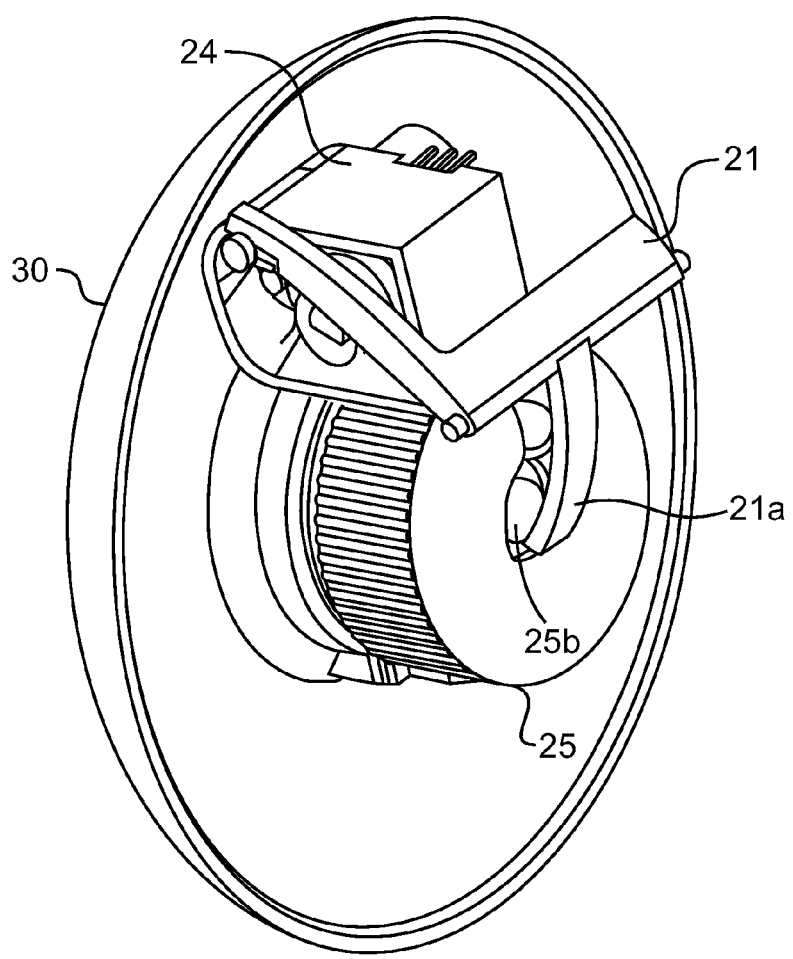

FIG. 11C shows the lever arm 21 pivoted forward thereby linearly pushing the piston cylinder toward the flange 30 in a "downstroke" motion. The lever arm 21 pushes the protrusion 21a against the alignment dome 25b of the piston cylinder 25 to move the piston cylinder 25 toward the nipple. As mentioned, the nipple is insulated by the vacuum chamber 60 of the flange 30 from direct contact with other components such as the piston cylinder 25. The motion of the piston cylinder 25 is controlled by the level arm 21 which sets the default position of the piston cylinder 25 within the tunnel 34 such that the piston cylinder 25 rests away from the breast when the pump is not in action. During operation, in the "upstroke" motion, the lever arm 21 pivots back thereby releasing the piston cylinder 25 and the top 35 of the flange 30. The movement of the piston cylinder 25 is rather short, delicate and efficient in comparison with the pumping action of other breast pumps.

The servomotor mechanism 24 activates the rear-piston lever-arm system 100 embodied in the lever arm 21 and the piston cylinder 25 to create the "downstroke" action inward (toward the breast). This downstroke action displaces the air in the flange 30 which exits via a one-way valve 140 (See FIG. 17) that is inserted into the outlet 62, thereby releasing the vacuum and actively stimulating the breast for further expression of milk. In addition, milk expressed by the breast flows out also through the one-way valve 140 and into a collection bag 300 (as will be explained further herein). The "upstroke" action not only moves the lever arm 21 and the piston cylinder 25 back into their start positions, but also generates the vacuum pressure against the breast. The upstroke and down-stroke action of the system 100 alternatingly generates and releases the volume displacement vacuum in the chamber 60, and in particular in the flange 30. Among the features of this construction, the "upstroke" passively maintains or creates the vacuum via the vacuum chamber 60 of the flange 30 elastically returning to its normal state, and not by any energy expended by the servomotor mechanism 24. However, in other embodiments, the protrusion 21a may be linked to piston cylinder 25 and the top 35 so as to actively generate both the "upstroke" and "downstroke" motions of the vacuum chamber 60.

In order to further simulate the suckling motion of an infant, the preferred suckling time to releasing time is, for example, approximately 3:1 in a cycle of a second. Namely, the suckling stage takes ¾ second, and the releasing stage takes ¼ second for each cycle. However, other cycling ratios may be used based on individual user preferences or breast-feeding requirements. The combination of the servomotor mechanism 24, the lever arm 21 and the piston cylinder 25 provides precision control of the air compression inside the chamber 60 which allows the precise controlling of the cycle rate and the vacuum level.

Figure 12:
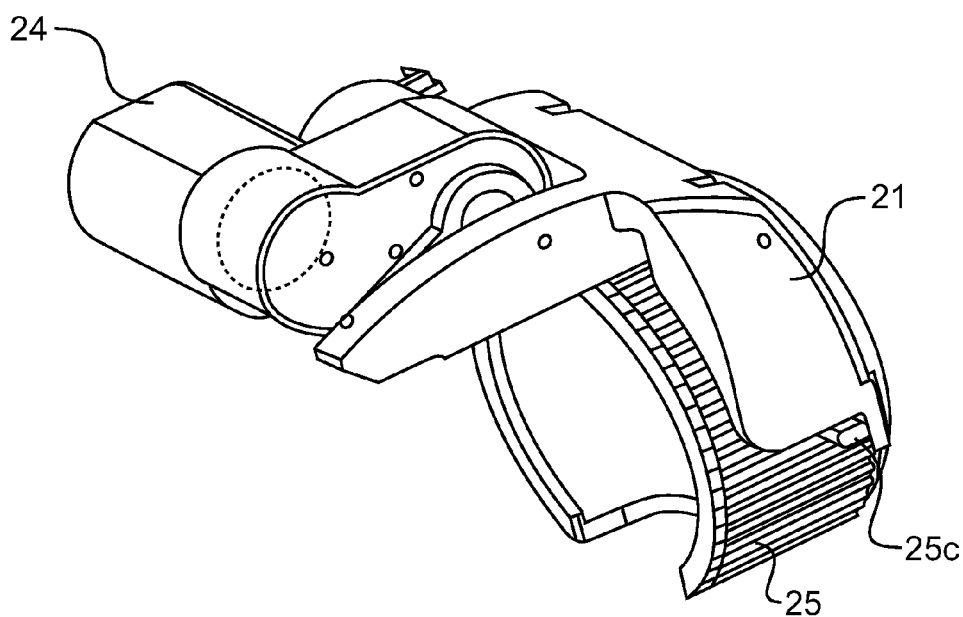
FIG. 12 shows a second embodiment of a rear-piston lever-arm system in conjunction with a servomotor mechanism of the breast pump according to the first embodiment.

In a second embodiment of the rear-piston lever-arm system 100, as shown in FIG. 12, the lever arm 21 is formed to surround the side wall of the cylinder piston 25 and connect to the piston via a protrusion 25c formed on the side wall. When the lever arm 21 pivots, it rotatively pushes on the protrusion 25c (rather than push on the top 35 of the piston cylinder 25) thereby linearly moving the cylinder piston 25. Otherwise, the operation and effects of this second embodiment are the same as those of the first embodiment.

Figure 13:
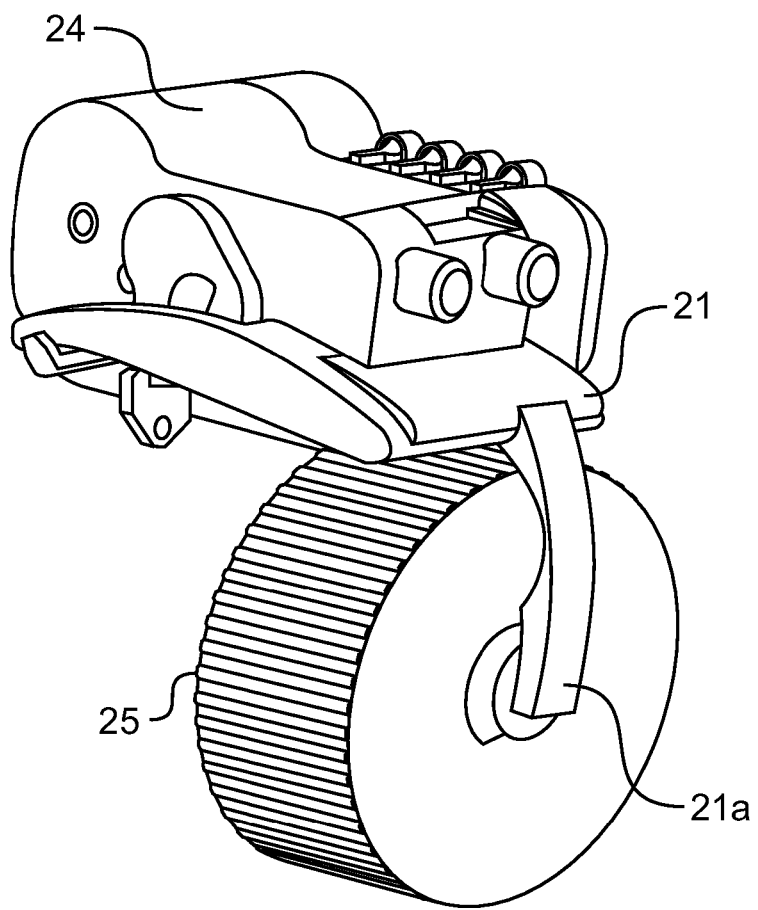
FIG. 13 show a third embodiment of the rear-piston lever-arm system in conjunction with another embodiment of the servomotor mechanism according to the invention.

As shown throughout the drawings, the present invention includes various embodiments for the servomotor mechanism 24. FIGS. 11A-C depict using a first embodiment of servomotor mechanism 24, while FIGS. 5 and 12 illustrate a second embodiment of the servomotor mechanism 24 that is used with the rear piston 25 and the modified lever arm 21. FIGS. 6 and 13 shows a third (preferred) embodiment of the servomotor mechanism 24 applied to a third variation of the lever arm 21.

Figure 14:
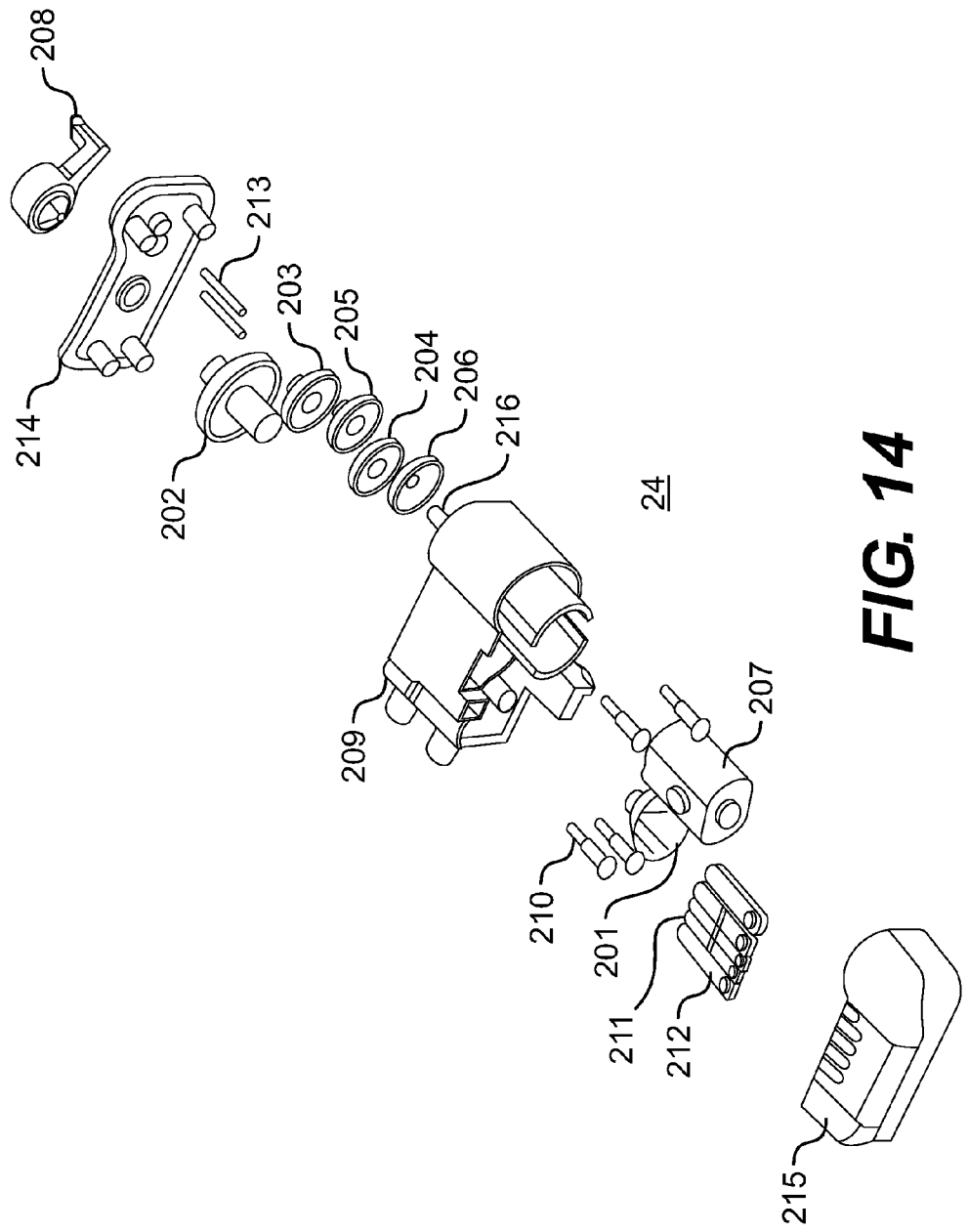
FIG. 14 is an exploded view showing the servomotor mechanism illustrated in FIG. 13.

FIG. 14 illustrates an exploded view of the third embodiment of the servomotor mechanism 24 so as to provide an example of the internal structure for a servomotor mechanism that would be applicable to the present invention. That embodiment is implemented via a structure that includes a potentiometer 201, an output gear 202, cluster gears 203-206, a DC motor 207, an arm 208, a motor housing 209, a screw 210, a rotary pot contact 211, a power contact 212, a gear train motor shaft 213, a front cover 214, a rear cover 215, and a pinion gear 216. Essentially, a servomotor mechanism for the present invention is implemented via mechanical or electro-mechanical system that pivotally moves a lever arm that then linearly moves a piston (in this case, a cylindrical piston 25) that then creates the pumping motion in the flange 30. The electric motor structure of the third embodiment (even of the first and second embodiments) as described above is one such system. Otherwise, given this disclosure of the invention, one of skill in the art should be able to devise other structures for a servomotor mechanism that would serve the purposes of the present invention and within the scope and intent of the claims.

Figure 16:
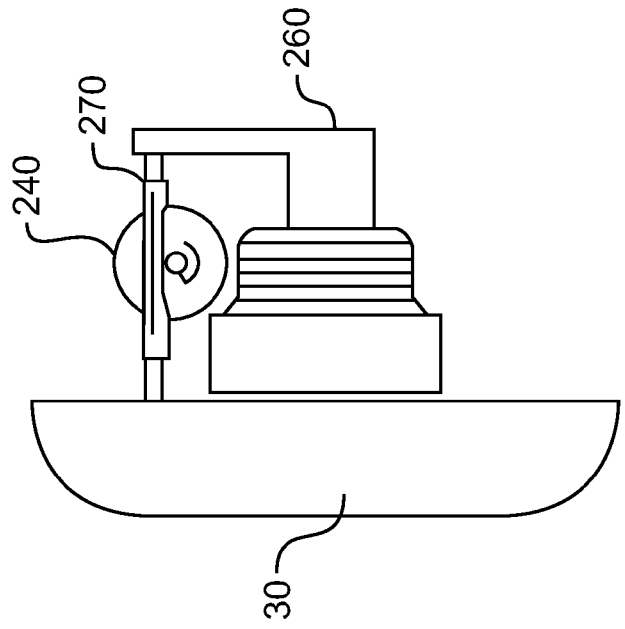
FIG. 16 shows a third embodiment of the linear movement mechanism according to the present invention.
Figure 15:
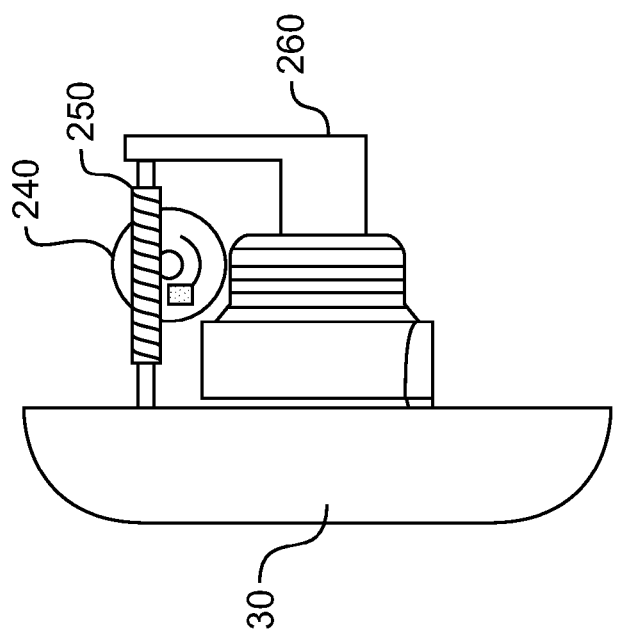
FIG. 15 shows a second embodiment of the linear movement mechanism according to the present invention.

FIGS. 15 and 16 illustrate other systems for providing the above-mentioned linear movements for the cylindrical piston 25, and thus the pumping operation of the flange 30. For example, FIG. 15 shows a lead screw mechanism with a rotary motor. The motor 240 oscillates at a cycle rate set by the user, and the vacuum level is controlled either by the user also, or by a microprocessor 90 (See FIG. 6) according to a predetermined stroke/suckling profile. The rotation of a lead screw 250 pushes a plunger 260 so as to push the top 35 of the flange 30 toward the breast. The reverse rotation of the motor 240 rotates the lead screw 250 away from the breast so as to move the plunger 260 away from the breast. This allows the flange 30 to return to its natural state so as to create a negative pressure in the vacuum chamber 60.

In FIG. 16, the lead screw 250 is substituted with a rack and pinion 270, wherein the motor 240 again oscillates at a cycle rate set by the user, and the vacuum level is controlled either by the user also, or by a microprocessor 90 (See FIG. 6) according to a predetermined stroke/suckling profile. The linear movement of the rack and pinion 270 pushes the plunger 260 pushing the top 35 of the flange 30 toward the breast. The reverse rotation of the motor 240 linearly moves the rack and pinion 270 away from the breast so as to move the plunger 260 away from the breast. Again, this allows the flange 30 to return to its natural state and create a negative pressure in the vacuum chamber 60.

Figure 17:
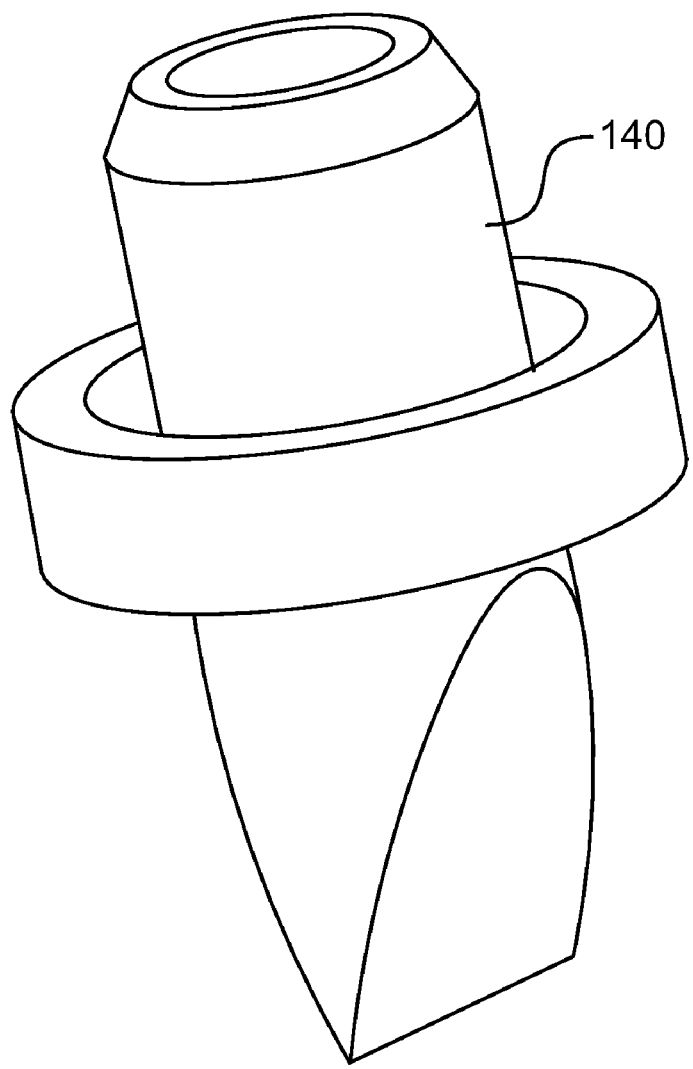
FIG. 17 shows a one-way valve for use with the breast pump of the invention.

The one-way valve 140 shown in FIG. 17 is used in conjunction with the outlet 62 of the flange 30. The valve is generally implemented as a one-piece element that is inserted into the outlet 62. Alternatively, the one-way valve may be constructed as an integral part of the flange 30. Its main function is to help maintain the vacuum in the chamber 60 during operation and to help draw the expressed milk away from the chamber 60 in the flange 30 so as to flow to a collection bag 300. However, other embodiments as those of skill in the art would understand may be accomplished used to implement the one-way valve 140.

Figure 18A:
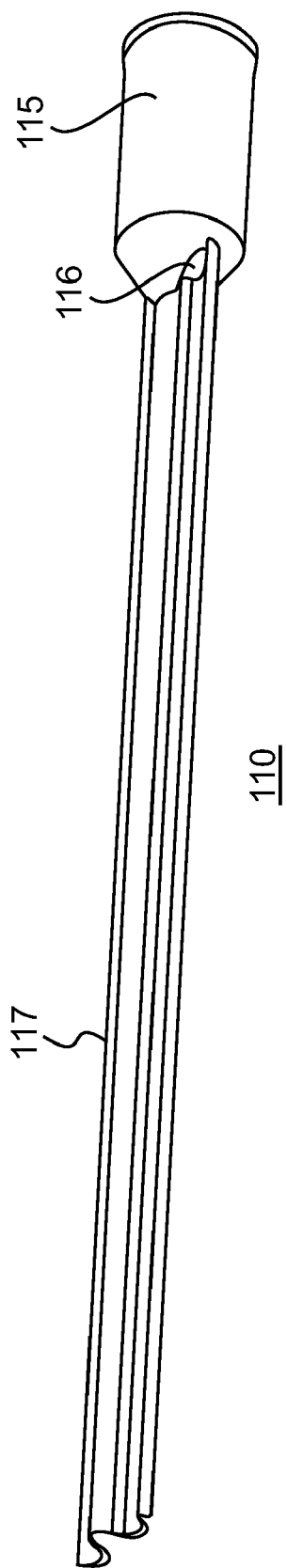

The splint 110 shown in FIG. 18A guides the milk from the pump to a collection bag 300. The splint 110 has a cup 115 and a wave-form portion 117. The cup 115 and the wave-form portion 117 of the splint 110 are inserted into the neck of the collection bag 300, extending downward to ensure the neck walls do not collapse due to the pressure from the bra at the point where the collection bag exits at the bottom edge of the bra (as will be discussed further hereinbelow). The cup 115 is formed to pressure fit into the outlet 70 of the housing shell 12 when inserted using an upward sliding force. The cup 115 is intended to have at least a liquid-tight fit within the outlet 70 while guiding the milk out of in the chamber 60. Preferably, the cup 115 has an air-tight fit when positioned in the outlet 70. Such a pressure fit is intended to hold the bag 300 tightly to the cup 115 so as to avoid any milk spillage and any air contaminants therebetween. At the bottom of the cup 115, there are holes 116 through which the milk is intended to flow out of the cup 115 and onto the wave-form portion 117 of the splint 110. In a preferred embodiment, the cup 115 has an extruded rim which will contact the outer edge of the neck of a collection bag 300 so as to further seal the neck. The splint may be formed integrally with the bag by incorporating the extruded tube in the construction of the collection bags. In such a case, a hot-pressed tear-off line is set between the end of the splint and the end of the bag neck.

Figure 18B:
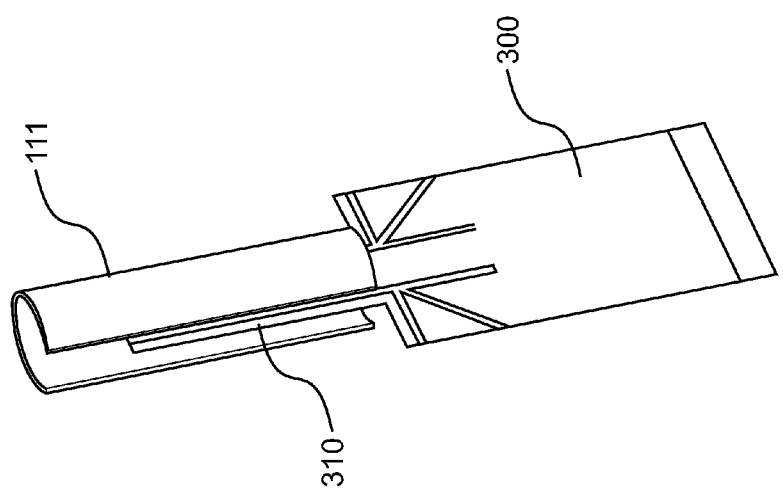
FIG. 18B shows an outer sleeve according to the present invention.

Also, in another variation as shown in FIG. 18B, an outer sleeve 111 is used to surround the neck 310 of the bag 300. The outer sleeve serves to protect the neck of the bag 300 as it extends from the pump to the body 305 of the bag 300. In this implementation, the neck 310 of the bag connects directly to the one-way valve 140 with the sleeve 111 surrounding the connection. In one form, the outer sleeve 111 is C-shaped in cross-section and also formed of a resiliently plastic material, which allows the sleeve to have some flexibility. Other cross-sectional shapes or configurations as would be understood by one of skill in the art to perform the same function as the C-shaped sleeve may be used.

When viewed along its longitudinal axis, the wave-form portion 117 has a substantially sinusoidal contour, wherein the peaks and valleys of the sinusoidal contour form channels along which the milk flows downward to the collection bag 300. The use of the wave form portion 117 enjoys several benefits over using a conventional tube form. First, it avoids any obstruction caused by air bubbles stuck in a tube. Second, a splint having a wave-form portion is more easily bent than a tube so as to conform with the contour of the breast and the bra to in order to reach the collection bag or a bottle. Third, the wave-form portion is easier to clean and keep sanitized than a tube. Plastic tubing needs to be cleaned each use. If washed, it has to be hung to allow it to drain and dry thoroughly. In contrast, the wave-form splint dries out more easily than a tube form. Lastly, a wave-form structure confronts less air resistance than a tube when it is inserted into either a regular container or the collection bag 300. As will be discussed further hereinbelow, the sub-assembly of the one-way valve 140 and the splint 110 provides further support for the vacuum chamber 60 so as to prevent it from collapsing.

Figure 19B:
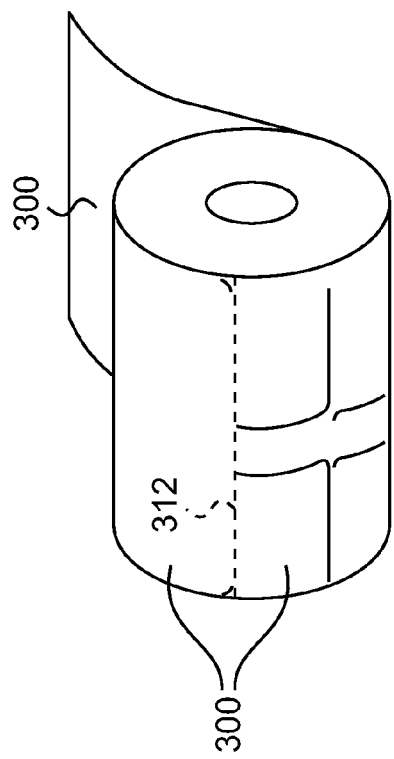
FIGS. 19A and 19B show a collection bag for use with the breast pump of the invention.
Figure 19A:
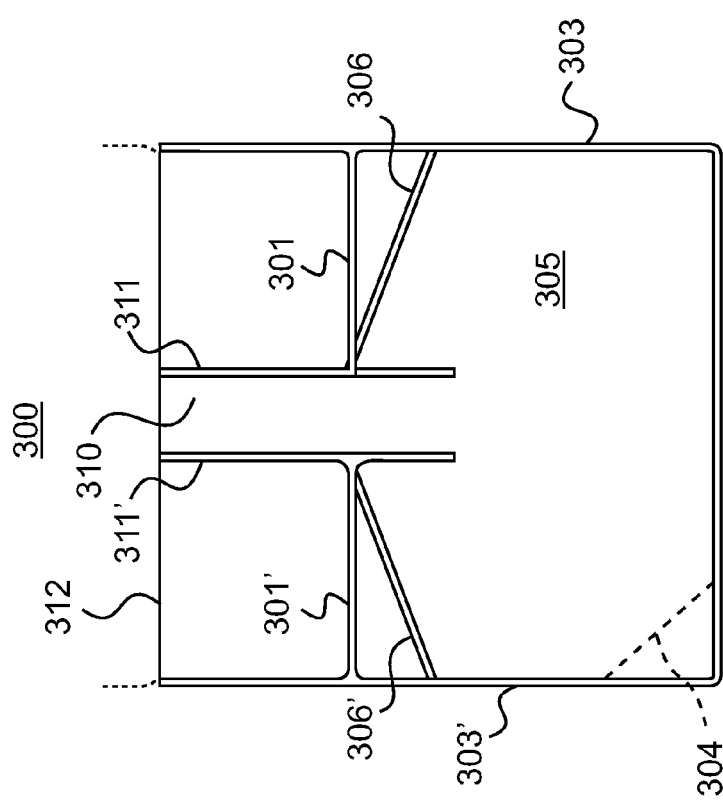

As shown in FIGS. 19A and 19B, the collection bag 300 is made of plastic and substantially deflated so as to be maintained in a substantially vacuum state for receiving the splint 110 and the milk. In one embodiment, the collection bag 300 is made by hot-pressing two thin plastic sheets to form a square bag body 305 with sealed edges 301, 301', 302, 303, 303' and a neck 310 with sealed edges 311 and 311'. Meanwhile, each perforation line 312 is punched with holes for easily separating the bags with a slight force. At the same time, graduations are printed on the surface of one plastic sheet to indicate ounces or milliliters. The sequentially hot-pressed bags are rolled into one roll to reduce storage space and make them easy to transport. Alternatively, the bags may be made using other conventional methods for fabricating plastic bags known in the art. Also, the bags may be formed into other shapes or with additional features (i.e., resealable tops, adhesive surfaces) or using other different materials that have the same manufacturing, sanitary and liquid-proof characteristics.

The sealed edges 311 and 311' of the neck extend into the bag body 305 so that the splint 110, including the cup 115, can be fully inserted inside the neck 310 to completely seal the splint inside the collection bag 300 thereby avoiding any milk spillage outside of the collection bag 300 during use. After the collection bag 300 is filled, a user can remove the splint 110 and roll the neck 310 so as to seal the bag. Further, adhesive tape or an adhesive surface formed on the neck 310 or the body 305 may be used to fixedly secure the rolled neck to the body of the bag.

In another embodiment, an additional pair of sealed edges 306, 306' in a V-shape are hot-pressed next to the neck 310 to provide additional pressure on the neck after the neck has been pressed from the top-down to expel any residual milk in the neck of the bag. In addition, the sealed edges 311, 311' include lower extensions that promote the sealing of the neck 310 when the neck is pressed, so as to function as a simple, one-way valve to prevent milk spillage after the neck is press-sealed. The neck of the collection bag with the sealed edges in a V-shape effectively becomes spill-proof after being pressed shut. This structure of the bag 300 solves the common problem encountered by mothers that use conventional plastic collection bags when they pump for breast milk. The plastic collection bags of the prior art have not been able to provide any effective means for sealing closed so as to allow the mother to put down the bags without spilling.

In a further embodiment of the invention, an additional tear notch 304 is hot-pressed at a corner of the bag so that a user may tear off the bag at the line to release the milk into another container to feed a baby. Additional tear notches are hot-pressed at the neck of the bag so that a user may alter the length of the neck by tearing off the bag at any one of the notches.

In a preferred implementation, each bag 300 is a freezer grade bag made of FDA rated plastic and intended only for single use so as to keep the milk from contamination caused by any residuals of old milk and eliminate laborious cleaning. The preferred dimensions of the bag body are 4.25 inches by 3 inches, and the dimension of the neck is 5.0 inches in length. The capacity of each bag is 4-8 ounces, which is the average production amount for a nursing mother. However, other dimensions may be used as one of skill in the art would understand.

Like breastfeeding, pumping is a learned skill. Most mothers are able to express only a few drops of milk when they first try a breast pump. Sometimes if mothers don't see milk immediately after beginning pumping, they start to pump harder or increase the suction with the mistaken idea that more pressure will "pull" the milk out. Doing this can cause discomfort and anxiety and actually discourage the let-down response. The invention is simple and easy to use so that the mother will intuitively become efficient at pumping without much practice and knowledge of how the breast works. In addition, many working mothers have no option but to pump in their offices or in a restroom. The privacy of using a conventional breast pump and the effect of the ambient air on the safety of the breast milk are at issue.

As generally illustrated in FIGS. 20A and 20B, a user just inserts a one-way valve 140 (if made as a separate component) into the hole in the flange 30 as a cap on the splint/bag. Otherwise, if the valve 140 is manufactured to be an integral part of the flange 30, then the user just then proceeds with inserting the "splint" 110 (the wave-shape guiding means) into neck 310 of a disposable collection bag 300. The splint 110 serves to keep the neck 310 of the bag fluid-passable as it passes underneath the bottom edge of the bra. The sub-assembly is inserted into the outlet 70 of the housing 12 at the bottom of the flange 30 and the breast pump 10. With the sub-assembly in place, the cup 115 of the splint 110 fixedly connects to the outlet of the one-way valve 140.

There is no need for the mother to undress herself in order to use the breast pump of the invention. In contrast, all the prior art requires a user to undress herself so as to use the pump.

After inserting the splint 110 into the housing shell 12, the user can insert the entire pump 10 with the sub-assembly of the splint 110 and collection bag 300 underneath her clothing and against the her breast. The inlet hole 50 is positioned over the breast so as to cover and surround the nipple and thereby catch the expressed breast milk. Alternatively, the user can insert the pump 10 underneath the clothing first, then insert the sub-assembly of the splint 110 and the collection bag 300.

In at least one embodiment, the insertion of the sub-assembly may be designed to act as an activation switch for the operation of the pump 10. Alternatively, either the slide button 16 or the push button 20 may be used as the activation switch, or a combination of the slide button 16 or the push button 20 in conjunction with the insertion of the sub-assembly. In an even further embodiment, the servomotor mechanism 24 may be activated by an initial movement of the switch 16 resulting from the insertion of the sub-assembly.

When a collection bag is filled or when the user is finished using the pump 10, the splint 110 along with the bag 300 is removed from the pump 10, but with the one-way valve 140 left in place to keep the outlet 70 plugged thereby prevent any milk from dripping out of the outlet 70. Upon removal of the sub-assembly, in one embodiment, contact between the sub-assembly and a switch of the servomotor mechanism 24 is severed which turns off the pump 10. As mentioned, the vacuum chamber 60 is air-tight and isolated from outside air turbulence. Such a design not only maintains the privacy of the user but keeps the pump from contacting any outside air contaminants.

With respect to the adjusting means 14 (See FIGS. 1A, 1B and 3), the pumping rate is controlled via a microprocessor 90 which reads the user inputs from the switch slide button 16 and the push button 20 for the vacuum level and the cycling rate, respectively, so as to power the servomotor mechanism 24 accordingly. The servomotor mechanism 24 in turn activates the rear-piston lever-arm system 100 to create a stroke action toward and away from the breast in accordance with the desired settings. When the appropriate time has passed, the microprocessor 90 will reverse the motor system to allow the flange 30 to return to its natural state. As noted above, the stroke action is programmed to mimic the natural suck-hold-release-relax cycling of a nursing baby according to the age of the baby. The present invention applies mimicking the baby's suckling movements to trigger a nursing mother's natural reaction to produce milk. The pumping rate in the present invention may be controlled and/or programmed to mimic both the nutritive and non-nutritive suckling actions of the a baby, which have distinctly different cycling characteristics.

Figure 21A:
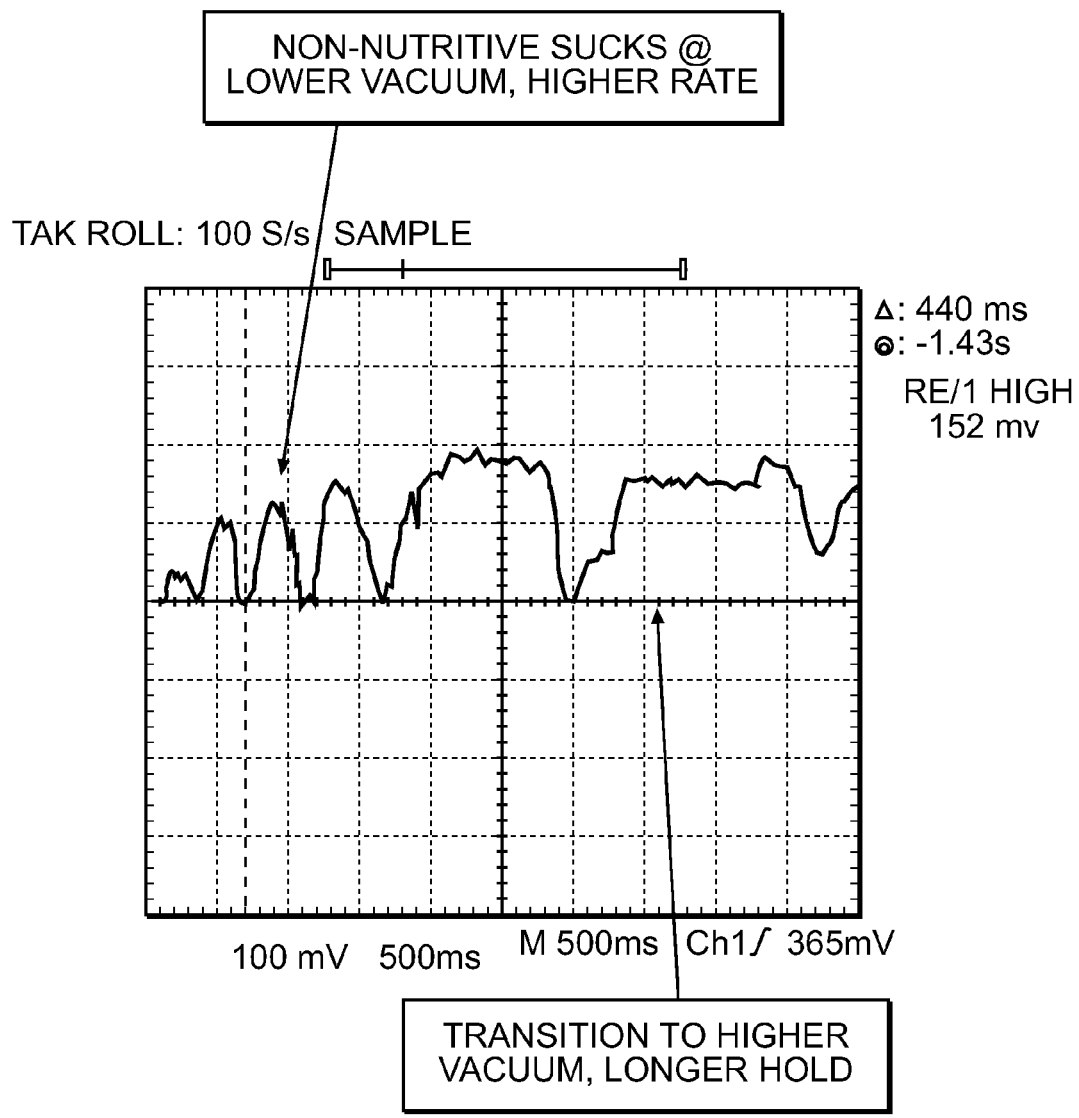
FIGS. 21A-C depict the actual suckling profiles of a seven-month-old baby boy.

According to a controlled study of a seven-month-old baby boy, the suck-hold-release-relax cycle starts with a series of non-nutritive sucks at low vacuum levels with a high suckling rate as the suckling pulses depicted in FIG. 21A. The non-nutritive suckling rate typically is higher than nutritive suckling; in this example, the non-nutritive suckling exceeded 100 cycles/min while nutritive suckling was 30-60 cycles/min The peak vacuum level of each suck increases until reaching a threshold for milk expression (the first and second nutritive sucks) then holds longer on the threshold (152 mmHg, in this case) than non-nutritive sucks with no plateau but mere a peak. The plateaus exhibit distinct flatness to hold the threshold vacuum level of each cycle. The holding period (in the plateau) is about 2-3 times of the relax period (drop from the plateau).

Figure 21B:
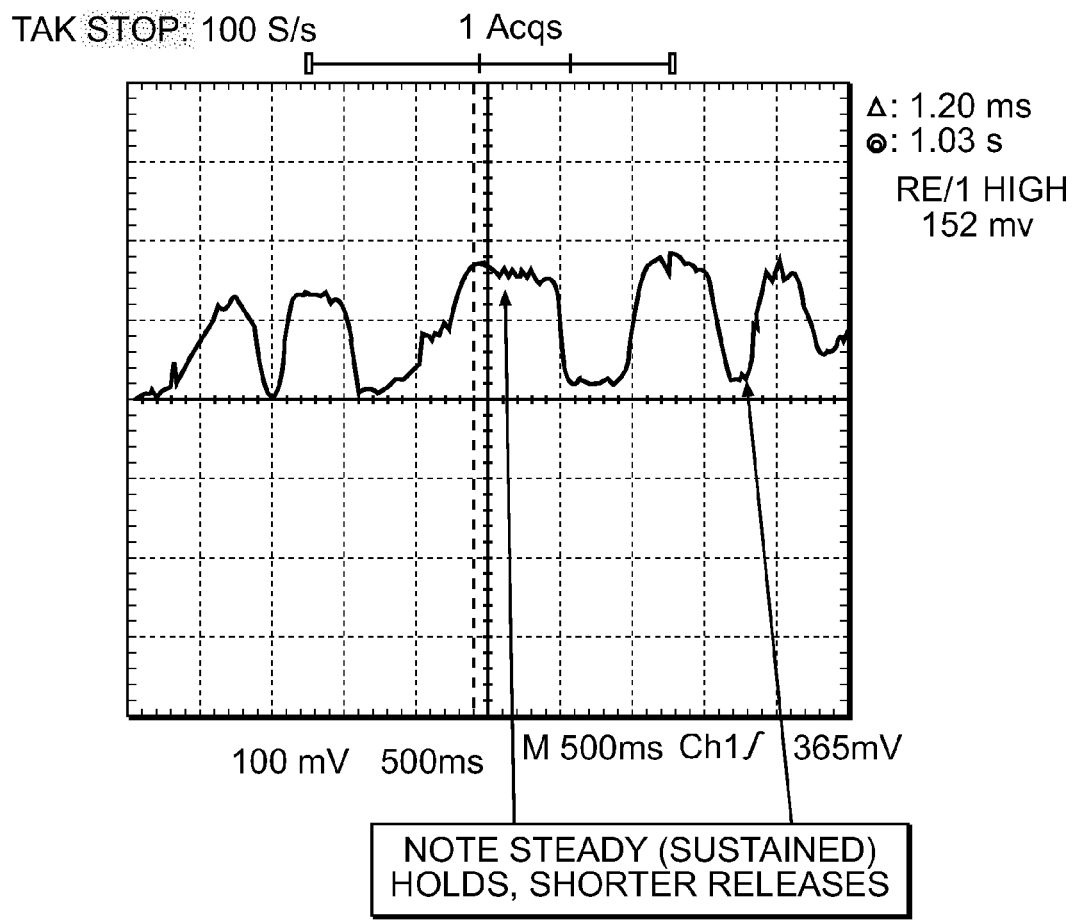
Figure 21C:
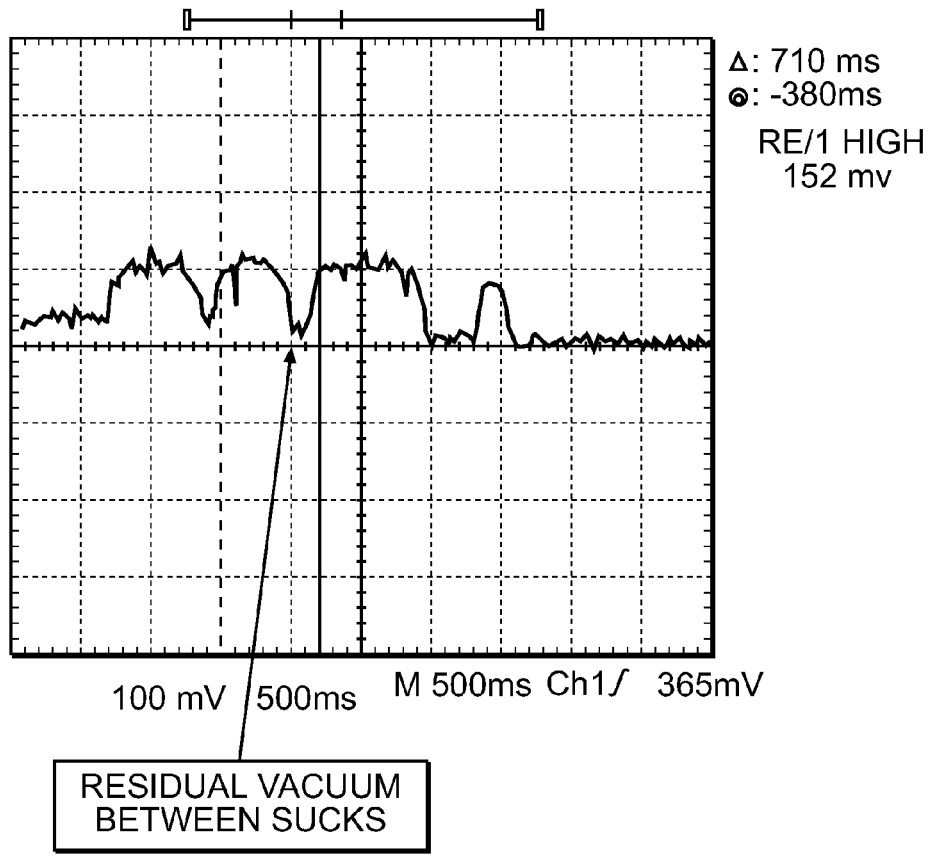

FIG. 21B shows a second example illustrating a steady-state post-ejection reflex action. Essentially, the baby has achieved a rhythm in suckling. FIG. 21C illustrates the threshold vacuum level decreasing with the cycle rate increasing. In this example, the baby is finishing feeding and/or tiring. Overall, the study reveals that the holding and releasing timing of a baby suckling is not symmetrical. Depending on the baby, there may be rapid transitions between holding and releasing periods. In the present invention, the microprocessor 90 is programmed to mimic the natural suck-hold-release-relax cycling of a nursing baby along the lines of the results of the study.

Figure 22A:
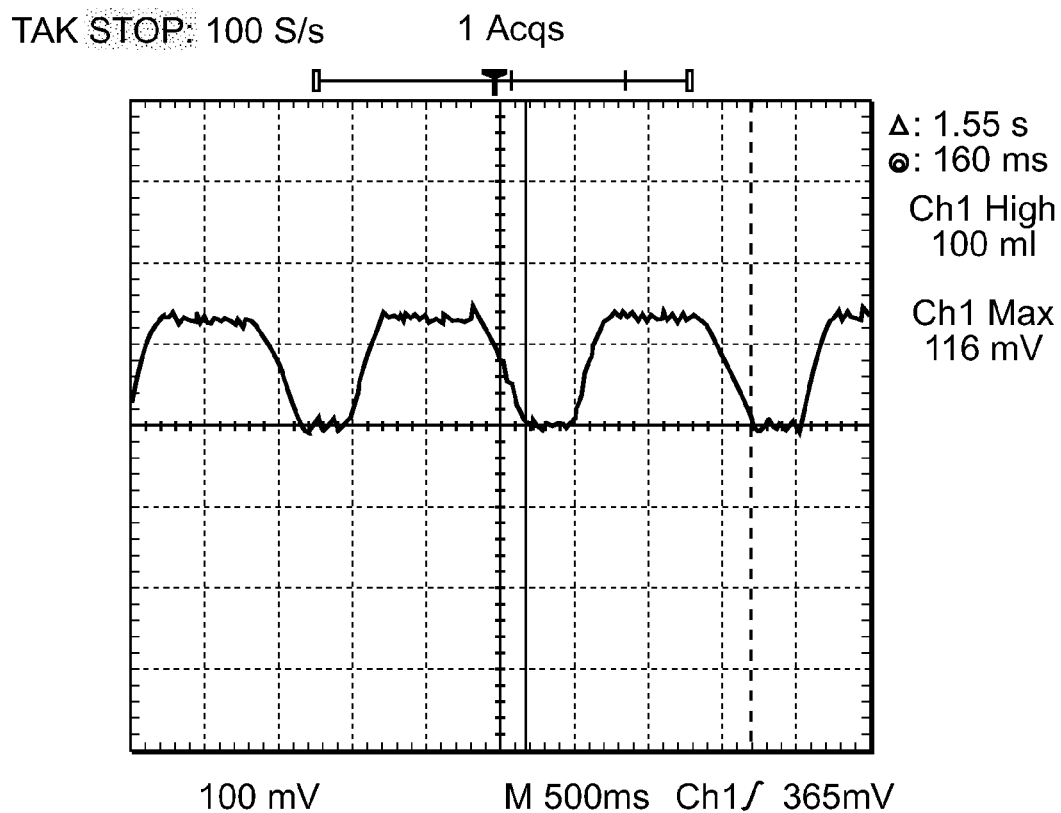
FIGS. 22A and 22 B depict the suckling profiles of the present invention.
Figure 22B:
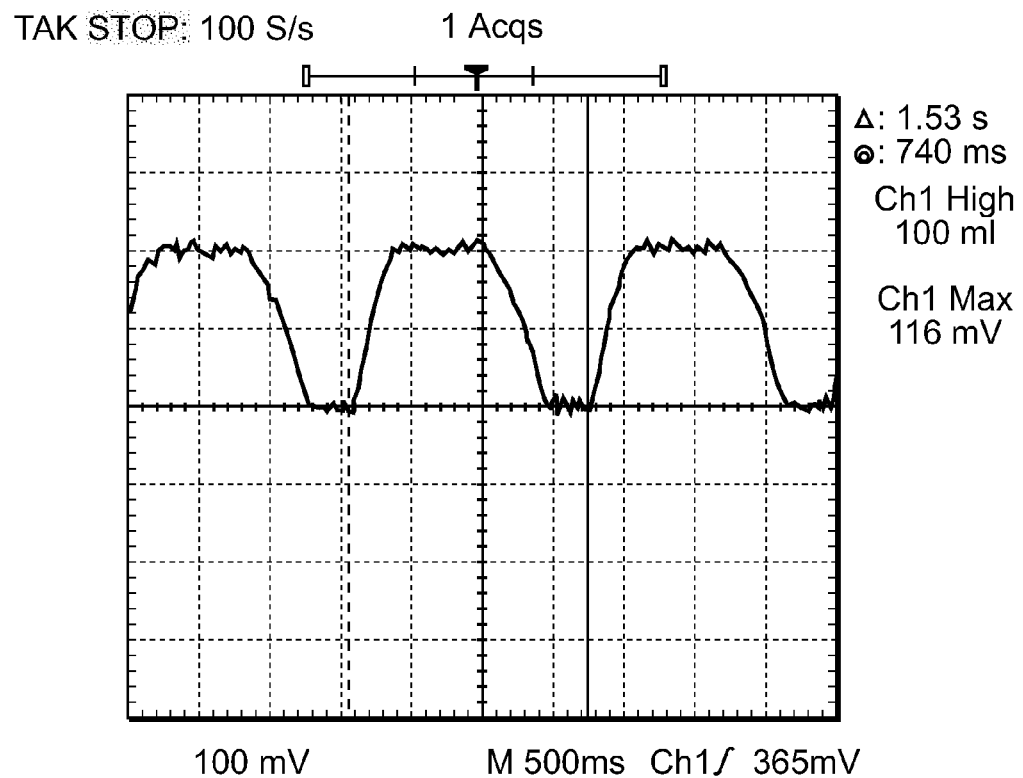

The microprocessor 90 may be programmed to suggest or control the vacuum level and the cycle rate. In one preferred embodiment, the microprocessor 90 is programmed with artificial intelligence so as to mimic the natural suck-hold-release-relax cycling of a nursing baby as discussed. Each stroke of the breast pump of the present invention has a definite holding period, which is about 2-3 times the relaxation period. As depicted in FIGS. 22A and 22B, the cycle profile is designed to be consistent regardless of the maximum vacuum level or the cycle rate settings.

In particular, the suction level starts at a minimum at the beginning for a new nursing mother, and then some quick, short pulses at the start of the pumping to especially stimulate and imitate more closely the way a baby initiates breastfeeding. Once the milk is flowing freely, long steadier strokes are initiated so as to be effective and less tiring. Since each woman has a different comfort level, the level may then be gradually increased to what is comfortable for her. The pumping mechanism supports a cycle rate up to 80 cycles per minute, which is higher than most of the other portable breast pumps (25-60 cycles/minute). However, the preferred cycle rates range from 35-60 cycles per minute which balances the efficiency and the comfort of the user. The most preferred cycle rate (45 cycles/minute) takes less than one-quarter second to fully vacuum the chamber 60 and incurs minimum noise.

This stroke action creates a vacuum on the order of 200 mmHg in the flange 30 while the one-way valve 140 seals off the opening. As shown in FIGS. 22A and 22B, when the maximum vacuum level is set at 136 mmHg, the matching cycle rate is 39 cycles/min when the maximum vacuum level is set at 204 mmHg, the matching cycle rate is 36 cycles/min. Vacuum control circuitry is provided for allowing manual adjustment of the level of vacuum generated by the electric pump means. This is accomplished by controlling the stroke length of the servomotor mechanism. In another embodiment of the invention, some residual vacuum is programmed in the stroke profile.

In another variation of the invention, a flow sensor may be connected with the adjusting means 14 to monitor the suckling results of the stroke actions.

Figure 23:
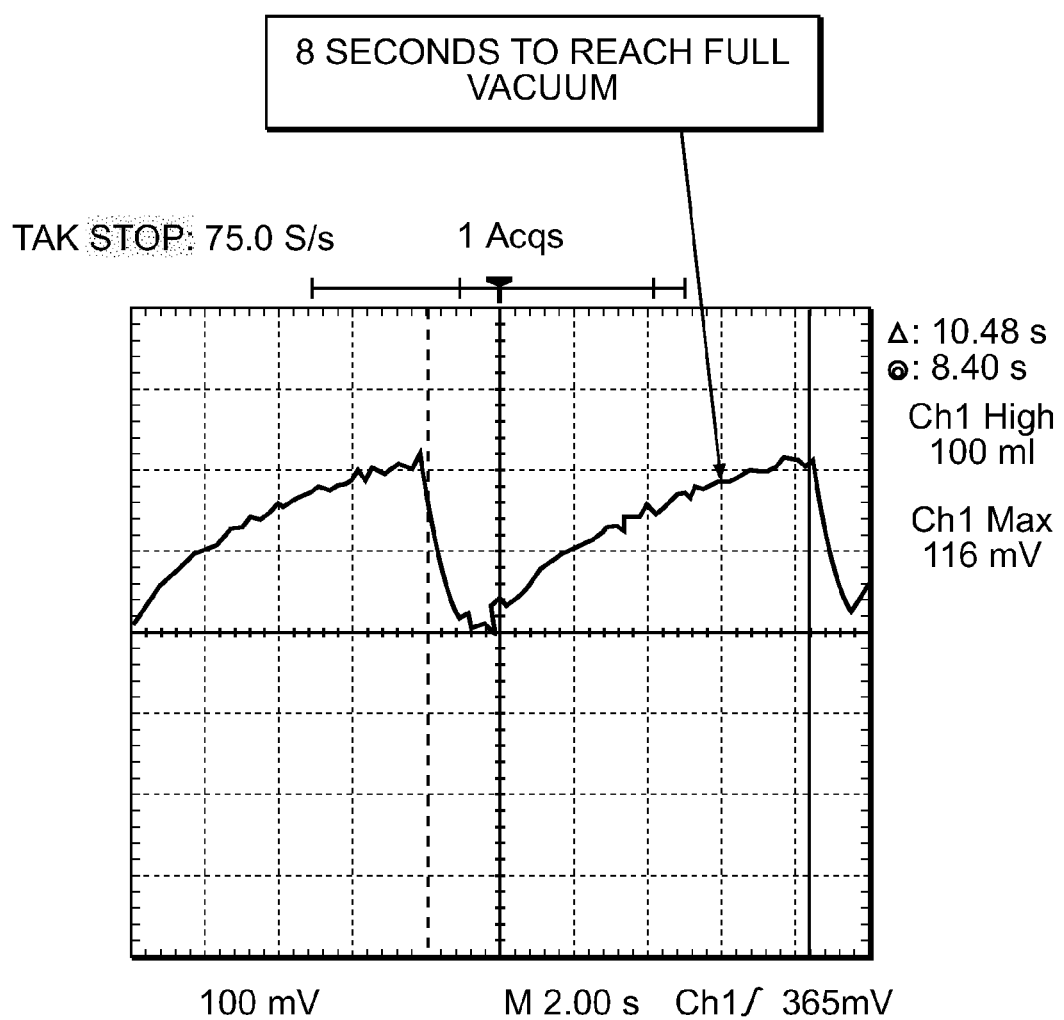
FIG. 23 depict the suckling profiles of a conventional, mass-retail double pump set.
Figure 24A:
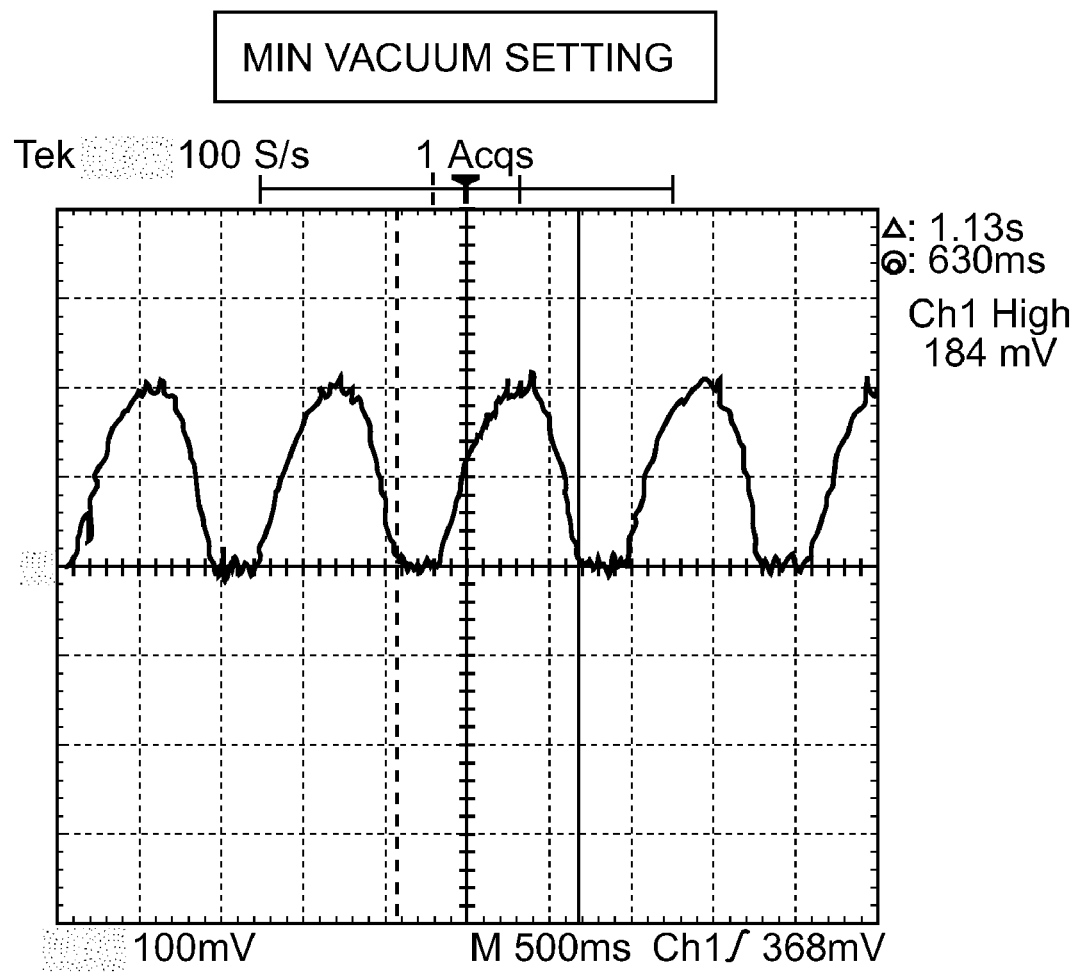
FIGS. 24A and 24B depict the suckling profiles of a conventional high-end double pump set.
Figure 24B:
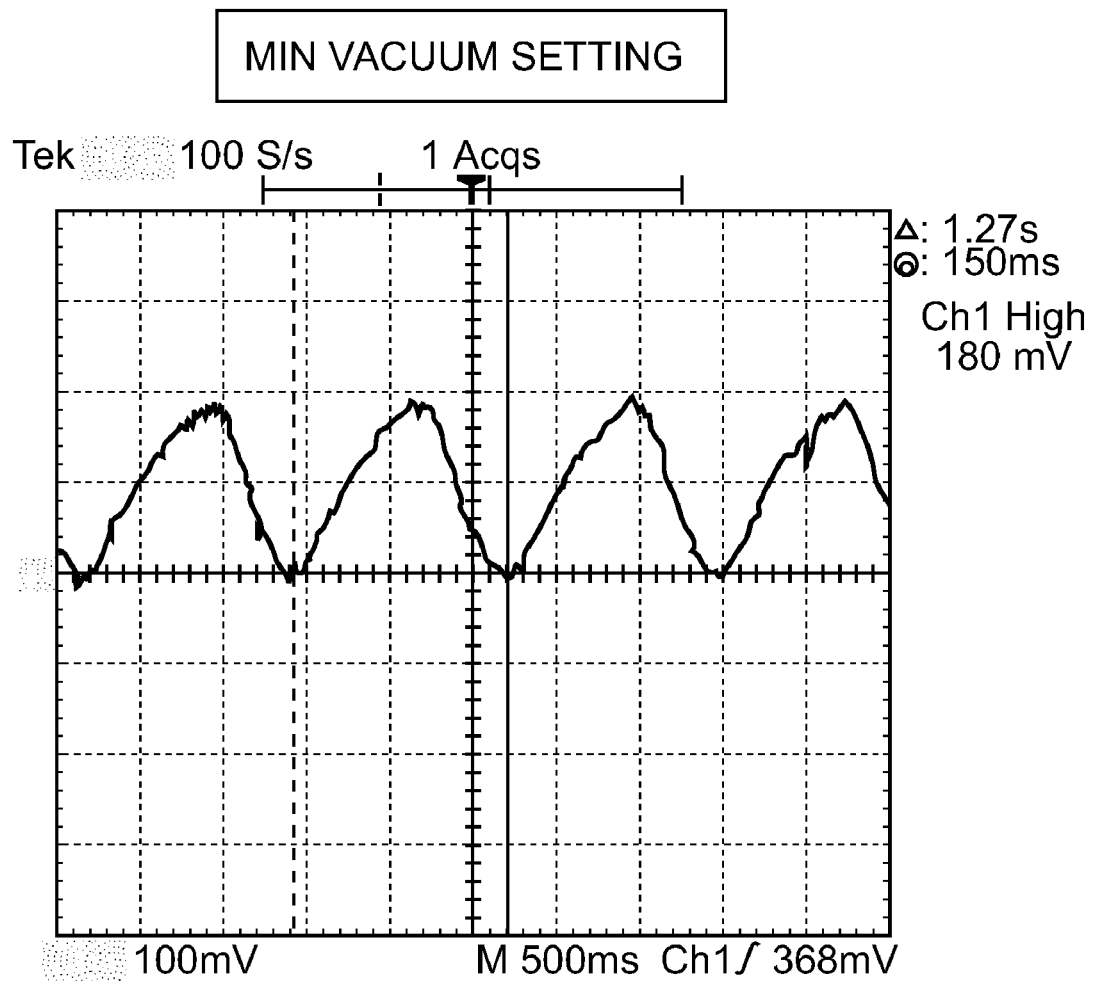
Figure 25A:
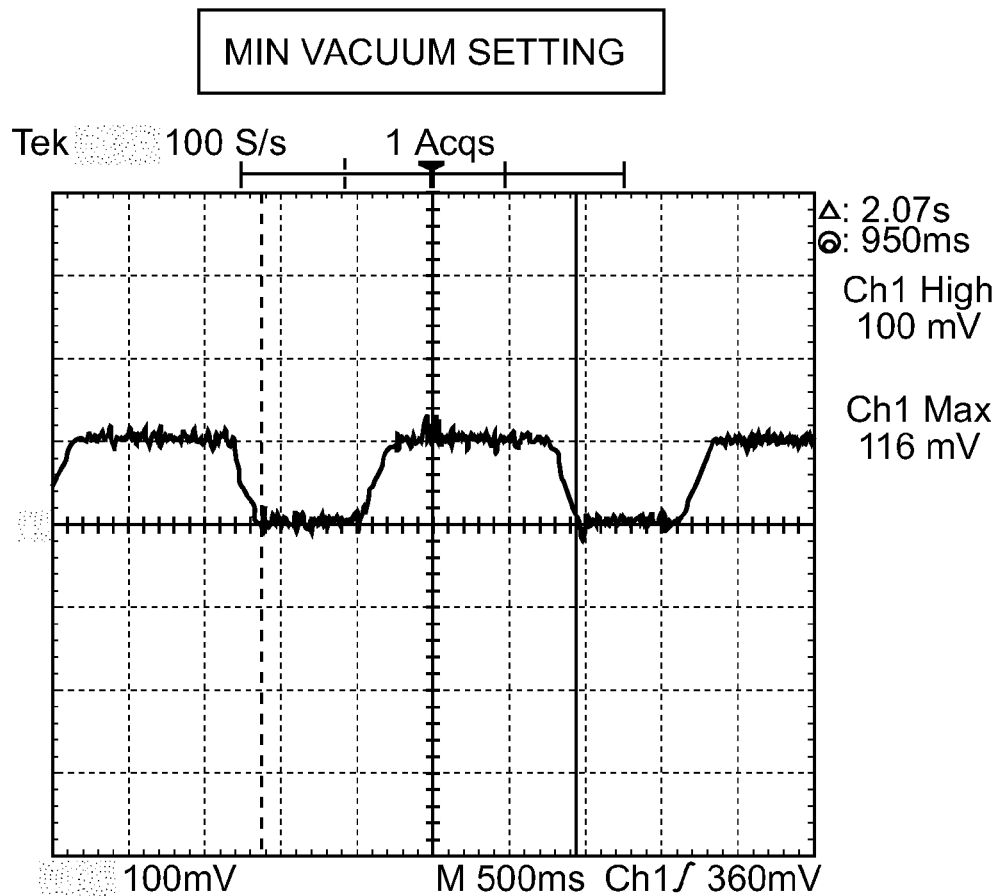
FIGS. 25A and 25B depict the suckling profiles of a conventional battery powered portable pump.
Figure 25B:
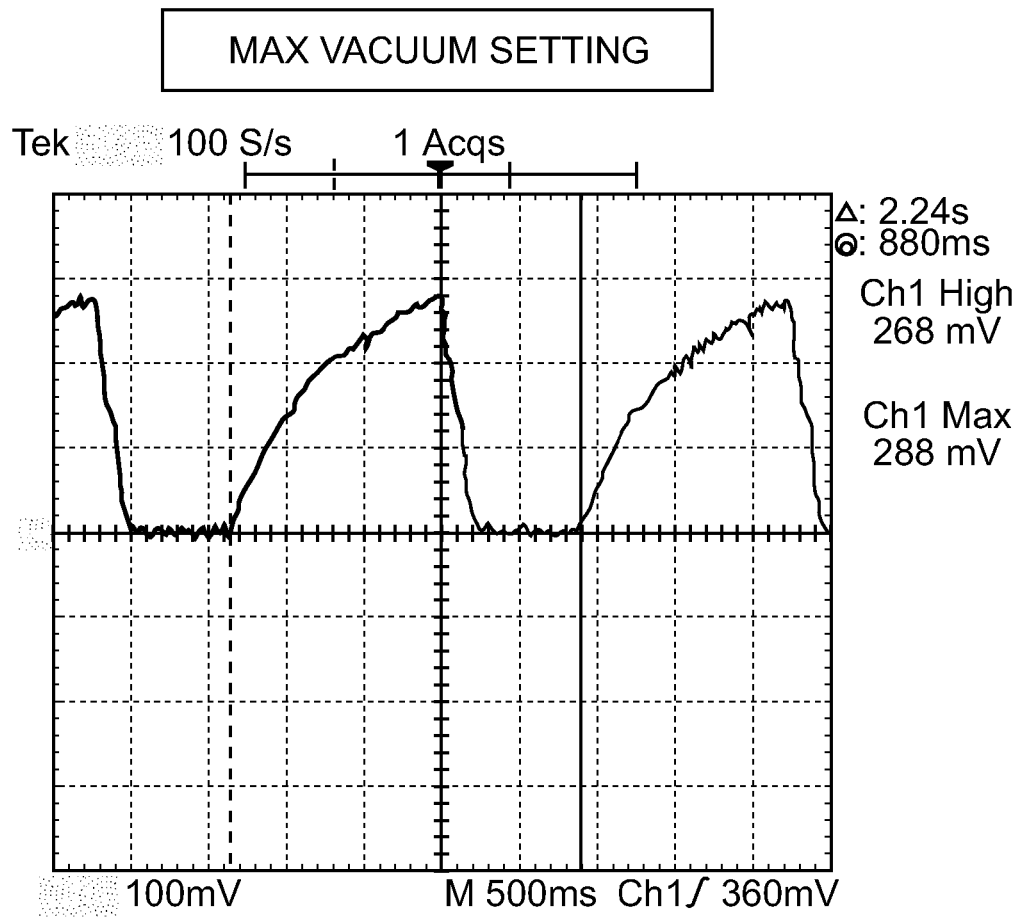

In contrast, the commercially available products simply operate under mathematics profiles rather than a natural baby suckling profile as the present invention. For example, the characteristics of one inexpensive, mass-produced double pump set allows manual control as well as residual vacuum as shown in FIG. 23. However, it operates with excessive tissue stress due to its slow vacuum rise profile. In addition, it operates terribly inefficient at 7 cycles/minute, which takes 8 seconds to reach the full vacuum level of 220 mmHg. Other conventional high-end double pump sets operate according to the profiles such as those shown in FIGS. 24A and 24B which are within appropriate vacuum levels (180-200 mmHg) at an appropriate cycle rate range of 47-53 cycles/min. Nevertheless, such systems have no holding periods, but instead release their vacuums immediately upon reaching full vacuum. One popular battery powered portable pump as shown in FIGS. 25A and 25B operates with appropriate holding periods (1-1.4 seconds) and releasing periods (0.9 second), but dragging along a slowly increasing profile from vacuum levels 100 to 270 mmHg at inefficient cycle rate range of 27-29 cycles/min. Such a profile yields long periods of stress on the breast to reach a excessively high vacuum level of 270 mmHg.

Studies and experience have shown that young breastfed babies usually need to nurse every 2-3 hours, and that it is best to pump on the same schedule. The more the breasts are stimulated, the more milk is produced. A good time for many mothers to pump is about one hour after the baby's first morning feeding. Most women tend to have more milk earlier in the day. The length of time spent pumping varies with each woman and with each day. When pumping one side at a time, alternating breasts several times during expression is more stimulating and can result in a higher volume of milk. Pumping at one side of the breast and nursing on the other side has the advantage of using the body's natural response to let down the milk for the baby.

The microprocessor 90 of the present invention may be programmed to suggest or control the timing for pumping. For example, using two pumps 10 simultaneously can cut the total pumping time in half. Double pumping may also result in better stimulation of prolactin due to its sense of balance provided to a nursing mother. In a double pump arrangement, the adjusting mechanism 14 of each pump may be linked by hardwire connection or by wireless link to coordinate or synchronize their strokes via the microprocessor 90.

Figure 26:
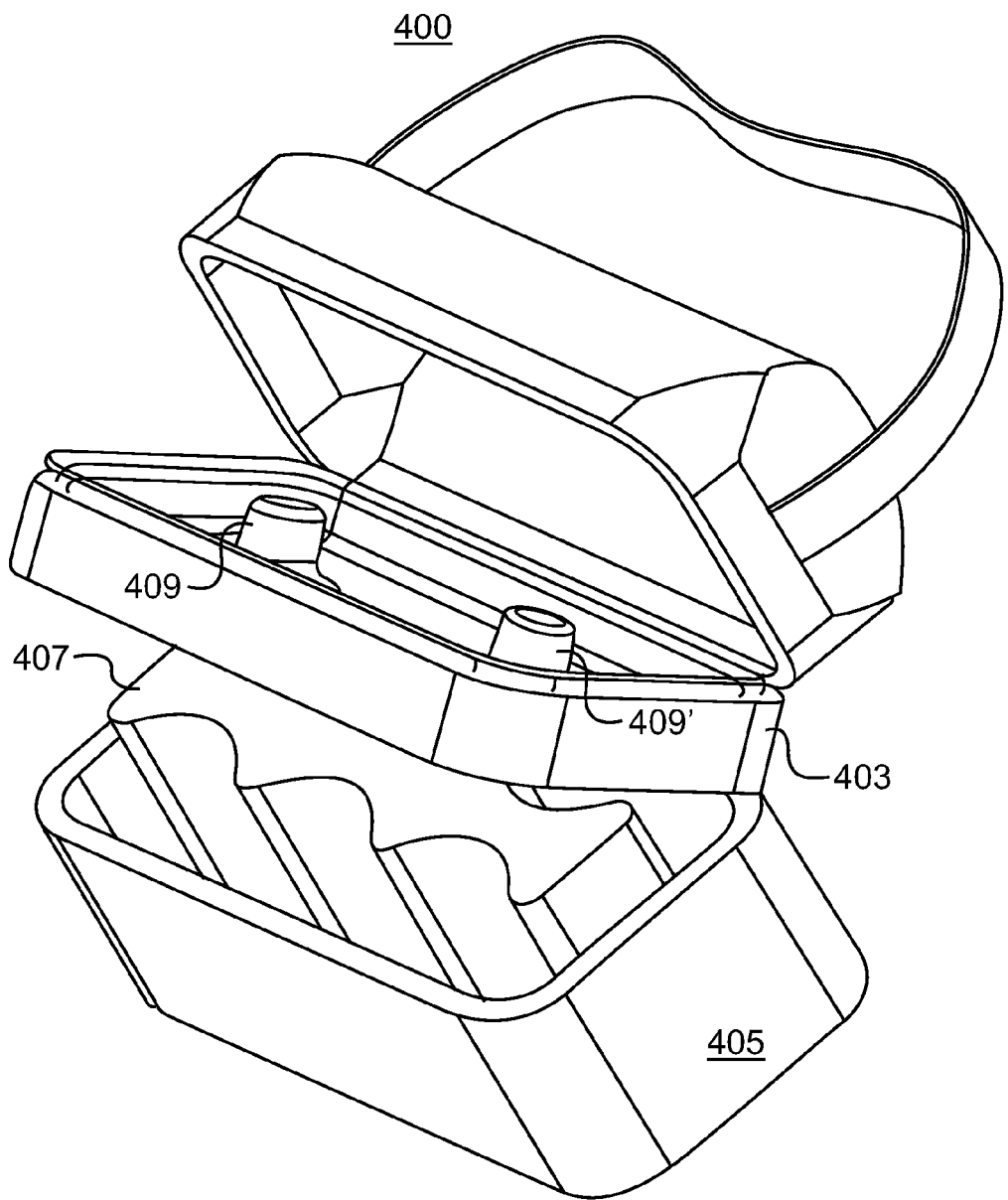
FIG. 26 shows a carrying case for a breast pump system according to the present invention.

A commercial implementation of the portable breast pump system of the invention as shown would include two breast pumps 10, a pair of valves 140 and splints 110, and a roll of collection bags. All of those components would be stored in a soft sided black shoulder bag 400 (FIG. 26) having two storage compartments, the upper compartment 403 includes a working surface for storage of the pumps on its breast pump holders 409, 409', the accessories, and complete instructions; and the lower compartment 405 includes heat-insulating side walls and at least one cooling element 407. The cooling element 407 is formed with concave seats for receiving collection bottles or bags. The closeness of the walls hold the collection bags next to the cooling element surfaces. The portable breast pump system of the invention would weigh only about 2 lbs., rather than the 8-10 lbs. of other commercially available portable breast pump system, or even then 25-40 lbs. of those used in hospitals. The cooler is available from Rubbermaid® (Blue ICE Model No. 1056). The shoulder bag 400 may be manufactured by companies such as California Innovation® with synthetic fabric surfaces which are easy to wipe clean. The aggregate weight of the cooler and the shoulder bag is approximately 2.5 lbs.

Parts of the pump such as the collection bags 300 are sterilized to FDA's hygienic standard for rubber articles before the first use, while other parts that come into contact with the mother's skin or the milk will need to be sterilized before first use. After initial use, only the flange 30, the valve 140 and the splint 110 need to be washed in warm, soapy water, rinsed with hot water and drained on a clean towel. However, periodic boiling for sterilization may be desirable, depending on the individual needs of the baby.

In summary, the breast pump of the present invention provides several unique features. As noted above, various parts of the system are made of plastic materials so as to be lightweight, easy to clean/maintain and easily conform with the contour of the user's breast (FIGS. 20A and 20B). Working moms can thus easily pump their milk and save it for the babysitter or daycare. The breast pump of the invention has very few parts so as to be easily assembled and cleaned. The overall system of the present invention also results in a breast pump smaller than commercially available breast pumps such as Hollister's Purely Yours™ Kit, i.e. about ¼ size of other portable (the shoulder bag actually is 70% smaller) and Medela's Pump in Style system.

The principles, preferred embodiments and modes of operation of the present invention have been described in the foregoing specification. However, the invention which is intended to be protected is not limited to the particular embodiments disclosed. The embodiments described herein are illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A system for collecting breast milk from a human breast forming part of a human body, comprising:
   a housing;
   a breast interface flange supported by the housing;
   a pump for generating intermittent pressure within the breast interface flange, the pump being carried by the housing;
   the housing, breast interface flange, and pump all being supported between a breast cup of a brassier worn on the human body with the housing facing the breast cup of the brassier and the breast interface flange facing the breast and forming an air-tight seal with the breast;
   the breast interface flange comprising an opening for delivering milk expressed from the breast through the opening;
   a milk collection receptacle in fluid communication with the opening comprising a container portion for receiving the expressed milk;
   wherein the housing, the breast interface flange, and the milk collection receptacle are supported by the brassier without the aid of hands or other support devices with the container portion of the milk collection receptacle supported below the brassier.

2. The system of claim 1, wherein the milk collection receptacle is a bag further comprising an elongated neck extending from the container portion and between a lower edge of the brassier and the human body while the brassier supports the housing, the breast interface flange, and the milk collection bag without the aid of hands or other support devices.

3. The system of claim 2, further comprising a milk conduit having a coupling end in fluid communication with the opening of the breast interface flange and a stem section received within the elongated neck of the collection bag, wherein the stem section extends between the lower edge of the brassier and the human body while the brassier supports the housing, the breast interface flange, the milk conduit, and the collection bag without the aid of hands or other support devices.

4. The system of claim 3, wherein the stem section of the milk conduit defines an elongated dimension and a narrow dimension, and the stem section defines an open wave shape across the narrow dimension.

5. The system of claim 4, wherein the container portion of the milk collection bag comprises first and second side panels and the milk collection bag comprises one or more seams sealing the first and second side panels together within part of the container portion of the milk collection bag to prevent milk contained within the container portion from leaking through the elongated neck when the milk collection bag is laid down horizontally on the first or second side panel without the milk conduit received within the elongated neck.

6. A system for collecting breast milk from a human breast forming part of a human body, comprising:
   a breast pump comprising a pump mechanism;
   a breast interface flange comprising a vacuum chamber having an interior volume, a collapsible bellows structure and a one-way valve, wherein the bellows structure repeatedly collapses and recovers a portion of the interior volume of the vacuum chamber in response to operation of the pump mechanism, while the one-way valve vents positive pressure within the interior volume of the vacuum chamber, to repeatedly create and release suction within the breast interface flange to impart a milking action to the breast;
   the breast interface flange supported between a breast cup of a brassier worn on the human body with the breast interface flange forming an air-tight seal with the breast;
   the breast interface flange comprising an opening supporting the one-way valve for delivering milk expressed from the breast through the opening;
   a milk collection bag in fluid communication with the opening comprising a container portion for receiving the expressed milk and an elongated neck extending from the container portion; and
   wherein the milk collection bag is supported by the brassier with the container portion of the bag supported below the brassier and the elongated neck extending between a lower edge of the brassier and the human body to the container portion of the collection bag while the brassier supports the housing, the breast interface flange, and the collection bag without the aid of hands or other support devices.

7. The system of claim 6, further comprising a milk conduit having a coupling end in fluid communication with the opening of the breast interface flange and a stem section received within the elongated neck of the collection bag, wherein the stem section extends between the lower edge of the brassier and the human body while the brassier supports the breast interface flange, the milk conduit, and the collection bag without the aid of hands or other support devices.

8. The system of claim 7, wherein the stem section of the milk conduit defines an elongated dimension and a narrow dimension, and the stem section defines an open wave shape across the narrow dimension.

9. The system of claim 7, further comprising a housing containing the pump mechanism and supporting the breast interface flange, wherein the housing is sized and configured to be supported between the breast cup of the brassier and the breast without the aid of hands or other support devices while the breast interface flange actively imparts the milking action to the breast.

10. The system of claim 9, further comprising a power supply for operating the pump mechanism contained within the housing.

11. The system of claim 10, wherein the container portion of the milk collection bag comprises first and second side panels and the milk collection bag comprises one or more seams sealing the first and second side panels together within part of the container portion of the bag to prevent milk contained within the container portion of the milk collection bag from leaking through the elongated neck when the container portion of the milk collection bag is laid down horizontally on the first or second side panel without the milk conduit received within the elongated neck.

12. A system for collecting breast milk from a human breast forming part of a human body, comprising:
   a housing;
   a breast interface flange supported by the housing;
   a pump for generating intermittent pressure within the breast interface flange, the pump being carried by the housing;
   the housing, breast interface flange, and pump all being supported between a breast cup of a brassier worn on the human body with the housing facing the breast cup of the brassier and the breast interface flange facing the breast and forming an air-tight seal with the breast;
   the breast interface flange comprising an opening for delivering milk expressed from the breast through the opening;

a milk collection receptacle in fluid communication with the opening comprising a container portion for receiving the expressed milk;

wherein the housing and the breast interface flange are supported by the brassier without the aid of hands or other support devices.

* * * * *